(12) United States Patent
Ariura et al.

(10) Patent No.: US 6,488,697 B1
(45) Date of Patent: Dec. 3, 2002

(54) APPARATUS FOR THERMOTHERAPY

(75) Inventors: Shigeki Ariura, Kanagawa-ken (JP); Haruo Ishiyama, Kanagawa-ken (JP); Michihiro Sugahara, Kanagawa-ken (JP)

(73) Assignee: Terumo Kabushiki Kaisha, Tokyo (JP)

( * ) Notice: Subject to any disclaimer, the term of this patent is extended or adjusted under 35 U.S.C. 154(b) by 51 days.

(21) Appl. No.: 09/614,587

(22) Filed: Jul. 12, 2000

(30) Foreign Application Priority Data

Jul. 13, 1999 (JP) .......................................... 11-199672
Jul. 13, 1999 (JP) .......................................... 11-199673

(51) Int. Cl.[7] ............................................. A61N 5/067
(52) U.S. Cl. ............................. 607/89; 607/88; 607/93; 606/17; 606/18
(58) Field of Search .................... 607/89, 100, 101, 607/88, 93; 606/10–34

(56) References Cited

U.S. PATENT DOCUMENTS

| 4,311,154 A | * | 1/1982 | Sterzer et al. ............... 607/102 |
| 4,672,963 A | | 6/1987 | Barken |
| 4,932,956 A | | 6/1990 | Reddy et al. |
| 4,932,958 A | | 6/1990 | Reddy et al. |
| 5,049,147 A | | 9/1991 | Danon |
| 5,207,672 A | | 5/1993 | Roth et al. |
| 5,292,320 A | | 3/1994 | Brown et al. |
| 5,496,308 A | | 3/1996 | Brown et al. |
| 5,509,929 A | * | 4/1996 | Hascoet et al. ............. 607/101 |
| 5,599,294 A | * | 2/1997 | Edwards et al. ............. 604/22 |
| 5,672,153 A | * | 9/1997 | Lax et al. .................... 604/22 |

FOREIGN PATENT DOCUMENTS

| EP | 0 673 627 | 9/1995 |
| JP | 07-95987 | 4/1995 |
| WO | 95/04934 | 4/1992 |
| WO | 93/04727 | 3/1993 |

* cited by examiner

*Primary Examiner*—Lee Cohen
*Assistant Examiner*—H M. Johnson, III
(74) *Attorney, Agent, or Firm*—Burns, Doane, Swecker & Mathis, LLP

(57) ABSTRACT

The controller 6 in the apparatus 10 for thermotherapy automatically computes the power P of the laser beam and the flow volume Q of the refrigerant forwarded to the main body 110 as the therapeutic conditions required for effecting the thermotherapy. The controller 6 delivers control signals to the laser beam generating device 2 and the refrigerant circulating device 4, depending on the therapeutic conditions obtained as described above. The therapeutic conditions thus set are displayed on the monitor 7 together with the input information introduced into the operating part 8. The controller 6 is further capable of automatically computing the therapeutic conditions required for effecting the thermotherapy based on the minimum distance d1 and the maximum distance d2 between the laser beam emitting terminal 111a, namely the surface of the surface layer 21, and the target site 30.

18 Claims, 22 Drawing Sheets

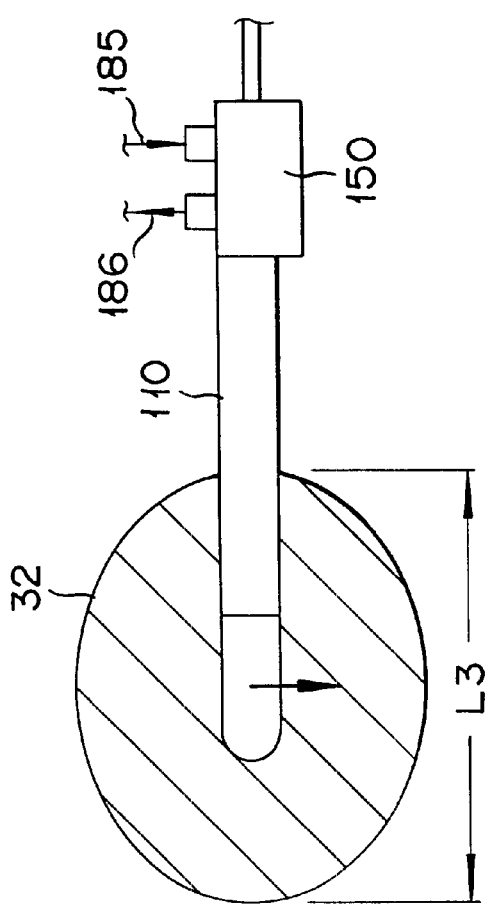
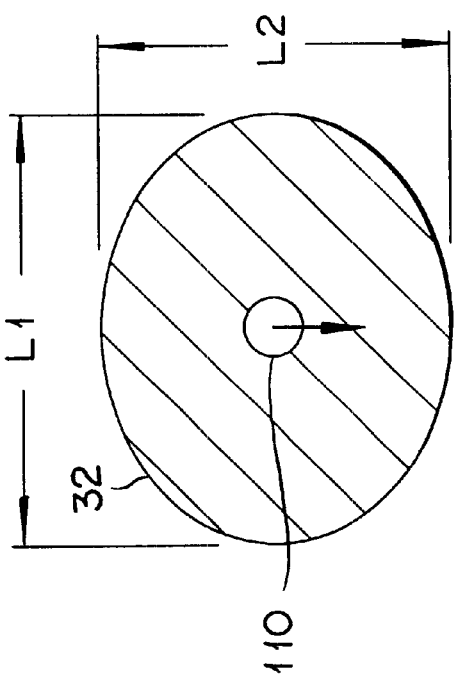

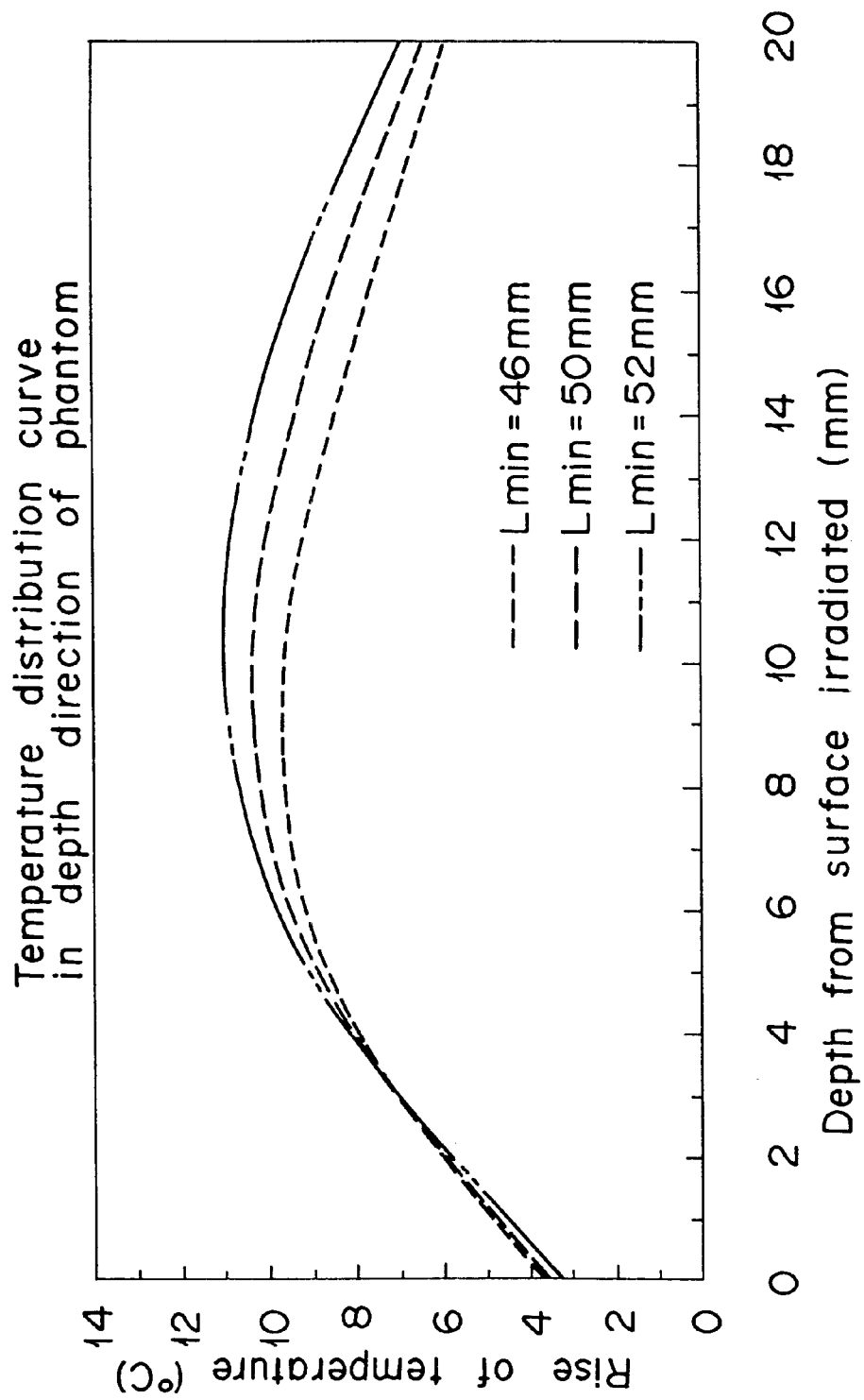

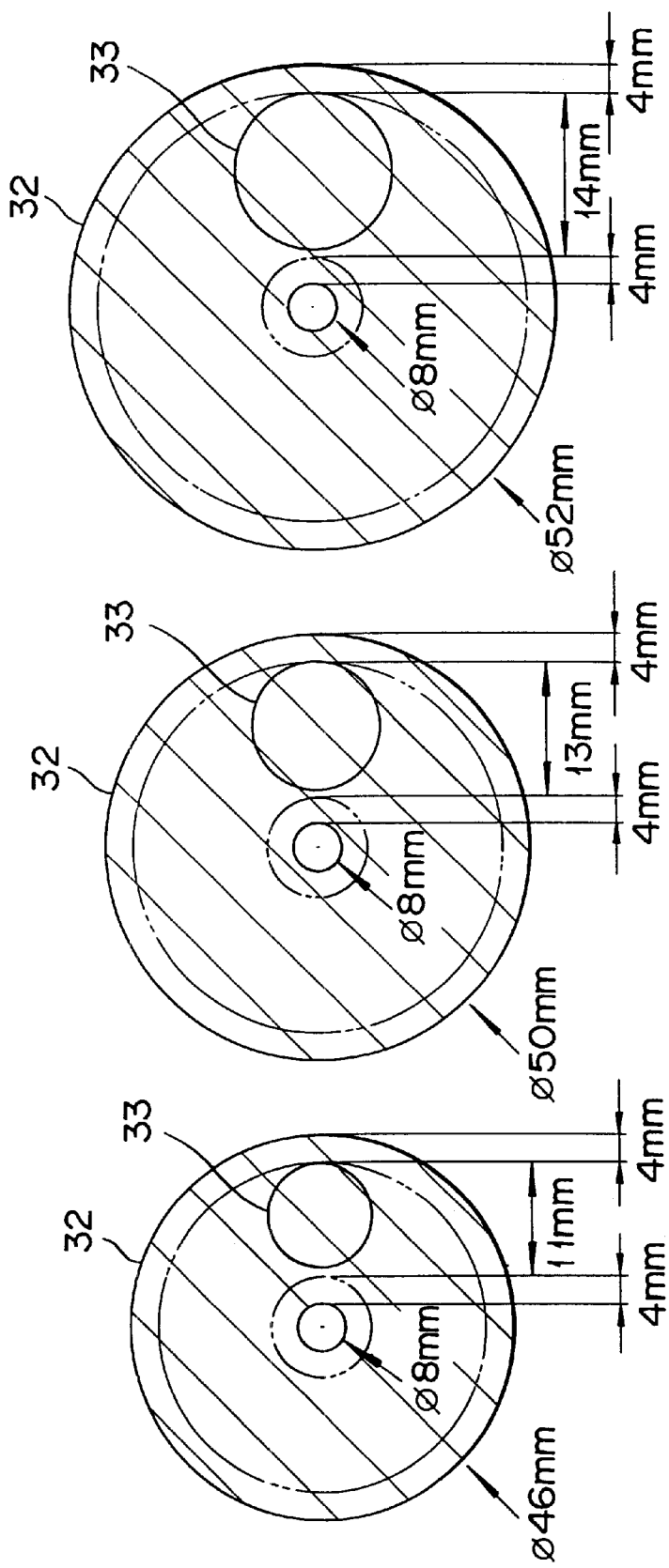

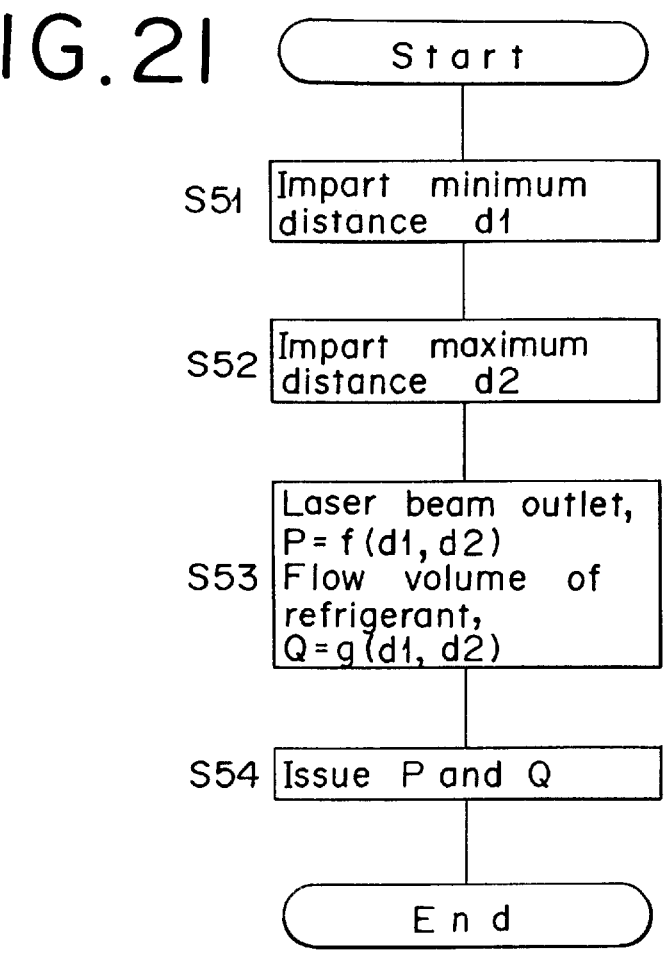
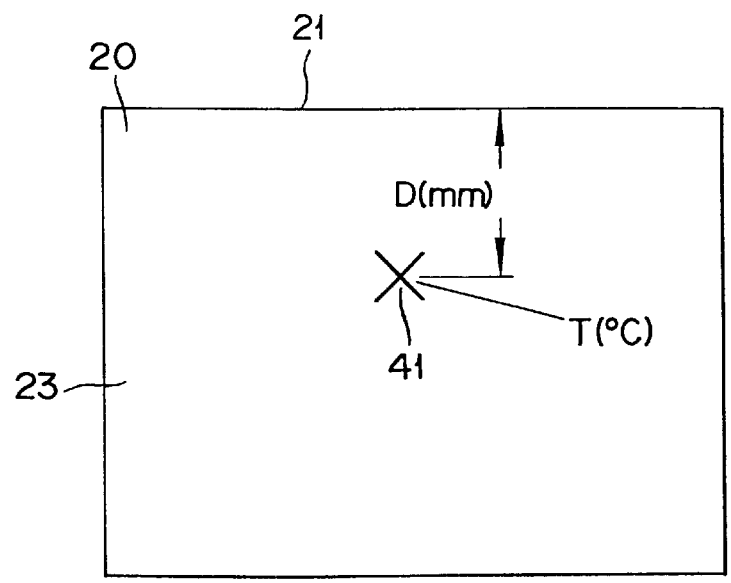

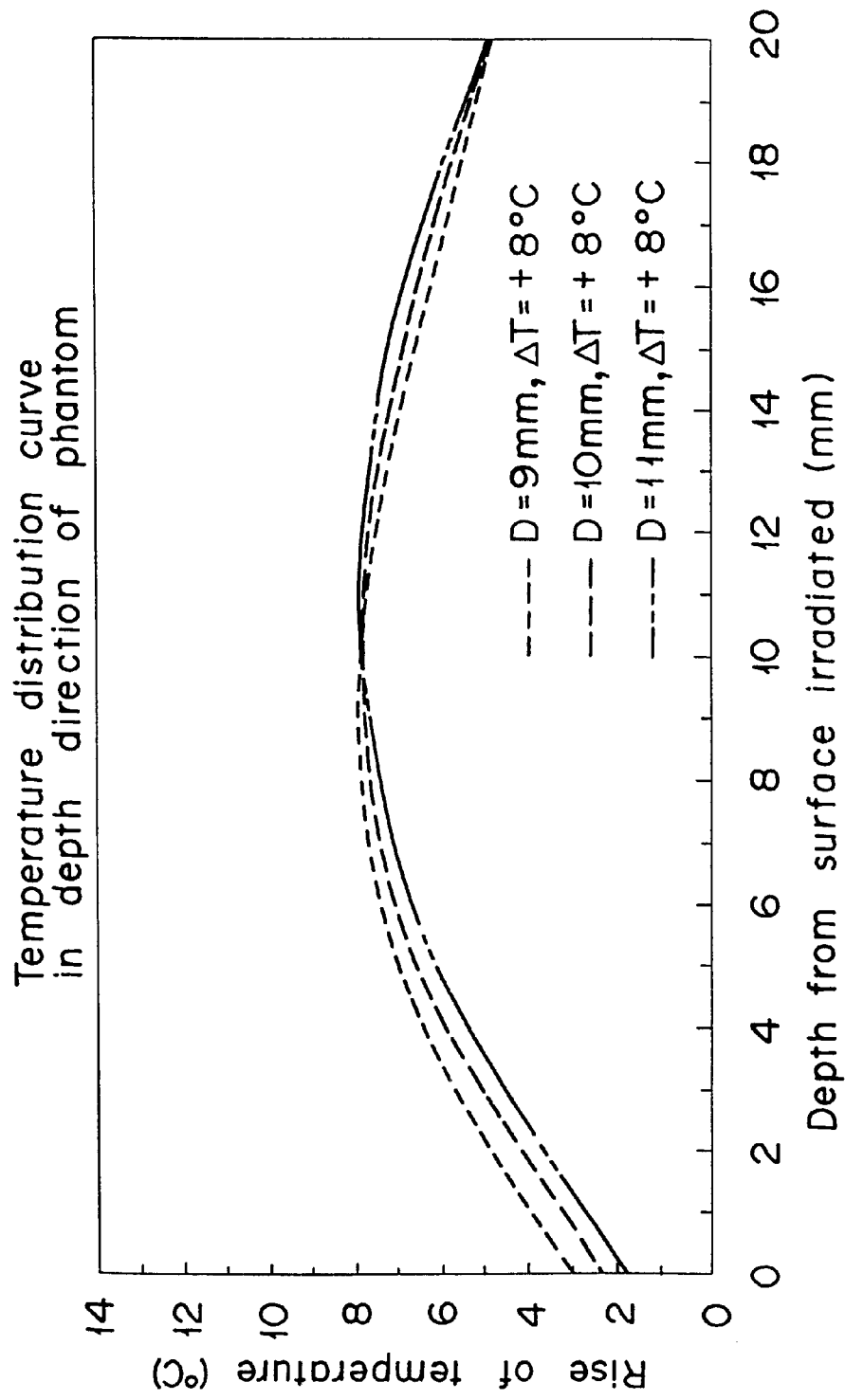

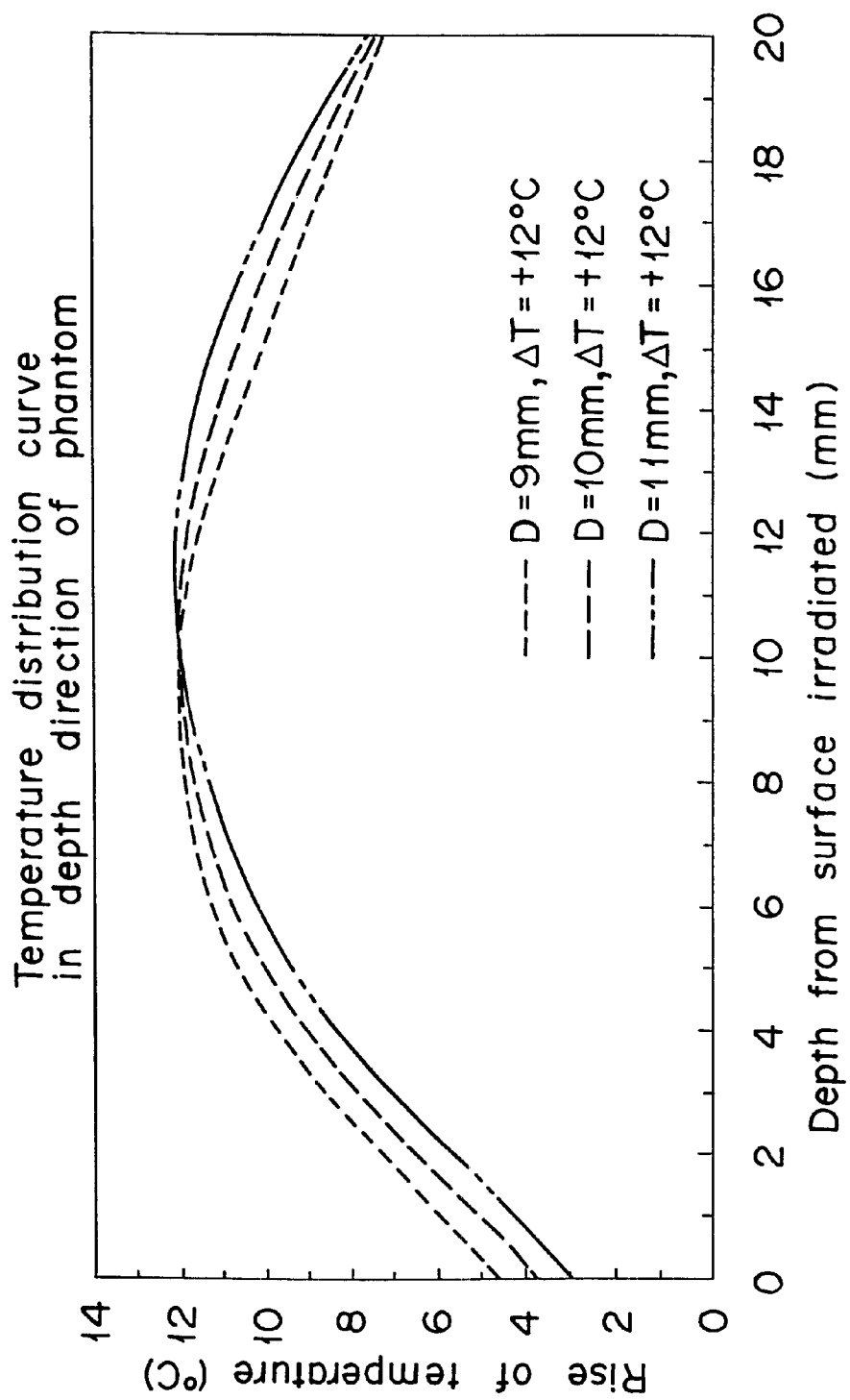

APPARATUS FOR THERMOTHERAPY

BACKGROUND OF THE INVENTION

1. Field of the Invention

This invention relates to an apparatus for thermotherapy with an inserting part inserted in a vital lumen such as, for example, a blood vessel, an urethra, or an abdominal cavity, or with an applying part surgically pressed against a vital tissue, or with an applying part pressed against a body surface and then irradiating a relevant vital tissue such as, for example, a prostate gland tissue with the energy from a laser beam, a microwave, a radio frequency, or an ultrasound which is released from an emitting part thereof disposed in the inserting part or the applying part.

2. Description of the Related Art

A known apparatus for thermotherapy of a given lesion site uses a long and slender inserting part adapted to be inserted into the living body via a lumen or a small incision artificially formed in the skin and irradiates tissue (e.g., prostate gland tissue) with energy, thereby eliminating the lesion site by inducing degeneration, necrosis, solidification, cauterization, or transpiration of the affected tissue.

This apparatus for thermotherapy is generally adapted to project the energy directly on the site of lesion located on the surface layer of the vital tissue or in the proximity thereof. The technique which, as in the thermotherapy of the prostate gland, irradiates the deep part of a vital tissue with the energy for the purpose of curing the site of lesion located in the deep part of a vital tissue, namely the site of lesion in the deep part, has been also known. Further, another known apparatus for thermotherapy has a heat source emitting part disposed on the leading terminal side of the inserting part with a refrigerant for cooling the neighboring tissue. According to this apparatus, the deep part of the vital tissue is concentrically heated while the neighborhood of the surface layer of the vital tissue in proximity to the emitting terminal of the inserting part is kept cooled and protected against possible heat injury.

In a conventional apparatus for thermotherapy, the therapeutic conditions are set by the following method. To be specific, the operator himself makes a judgment from his own experience in the selection of therapeutic conditions including, for example, the power of a heat source such as the laser, the duration of exposure to the heat source, the temperature of the refrigerant, and the flow volume of the refrigerant to be circulated. The operator then imparts these conditions to the apparatus.

In addition, a method which sets such therapeutic conditions as the power of a heat source by imparting to the apparatus the target temperature of a vital tissue of the lesion site (or the proximity of the lesion site) to which the long and slender inserting part thereof is inserted has been known (the official gazette of JP-A-07-95,987).

In the apparatus for thermotherapy mentioned above, however, it is generally difficult to estimate the approximate range of heating on the basis of the preset levels of the individual therapeutic conditions. The difficulty encountered in this estimation of the range of heating grows proportionally as the number of therapeutic conditions to be set increases.

The method which relies on the operator's judgment to set the therapeutic conditions, therefore, not only complicates the operation of imparting the therapeutic conditions but also entails the possibility of setting erroneous therapeutic conditions. Consequently, this method has the risk that the energy of heating will be so excessive as to inflict damage on the normal tissue in the proximity of the lesion site or that energy of heating will be so deficient as to prevent attainment of a sufficient therapeutic effect.

The method which relies upon imparting the target temperature of the vital tissue at the site of lesion or in the proximity of the site of lesion has the problem that the information concerning the size, position, and length of the site of lesion is not reflected in the therapeutic conditions to be set. Thus, when the energy of heating and the cooling are both excessive, for example, and even when the prescribed point in the site of lesion is allowed to reach the target temperature, the possibility arises that the range of heating will be so wide that the part to be heated will not be limited to the site of lesion but will be extended to the normal tissue in the proximity of the site of lesion and consequently the normal tissue may be damaged. When the energy of heating and the cooling are both insufficient, for example, and even when the prescribed point in the site of lesion is allowed to reach the target temperature, the possibility arises that the range of heating will be too narrow to attain the effect of therapy sufficiently. The possibility also arises that the part to be heated will deviate from the site of lesion and the effect of therapy aimed at will not be obtained satisfactorily.

SUMMARY OF THE INVENTION

One object of the invention is to provide an apparatus for thermotherapy which, depending on the morbid state of a patient, allows therapeutic conditions for effectively heating exclusively a given site of lesion to be set accurately and easily, and meanwhile prevents the normal tissue in the proximity of the site of lesion from sustaining damage.

One aspect of this invention concerns an apparatus for effecting thermotherapy of the prostate gland by exposing the affected vital tissue to an energy, the therapeutic conditions for the thermotherapy of the prostate gland being set based on input information including the data of diagnosis of the prostate gland.

Another aspect of this invention concerns an apparatus for effecting thermotherapy of the prostate gland by exposing the affected vital tissue to an energy, the therapeutic conditions for the thermotherapy of the prostate gland being set based on an input information including data for specifying the size of the prostate gland.

Still another aspect of this invention concerns an apparatus for effecting thermotherapy of the prostate gland by exposing the affected vital tissue to an energy, which apparatus comprises an input part for imparting to the apparatus input information including the data for specifying the size of the prostate gland and a control part for setting the therapeutic conditions for effecting the thermotherapy of the prostate gland on the basis of an input information imparted by the input part.

When the apparatus is constructed as described above, proper therapeutic conditions are automatically set by simply imparting to the apparatus input information including data for specifying the size of the prostate gland. The operation for the impartation of the input information is facilitated because the operator does not need to incur the trouble of judging from his own experience numerous therapeutic conditions to be set and imparting them one by one. Moreover, this construction can prevent the operator from setting erroneous therapeutic conditions. Depending on the morbid state of each patient, therefore, the apparatus is able to accurately and easily heat the site of lesion exclusively while preventing the normal tissue in proximity to the site of lesion from sustaining damage.

Another aspect of this invention concerns an apparatus for effecting thermotherapy by exposing the affected vital tissue to an energy, with the therapeutic conditions for the thermotherapy being set based on an input information including the position of a target heating site.

Still another aspect of this invention concerns an apparatus for effecting thermotherapy by exposing the affected vital tissue to an energy, which apparatus comprises an input part for imparting to the apparatus input information including data specifying the position of a target heating site and a control part for setting the therapeutic conditions for effecting the thermotherapy.

When the apparatus is constructed as described above, since proper therapeutic conditions are automatically set by simply imparting to the apparatus input information including position information concerning a target site which is a target site of heating, the operation for the impartation of the input information is facilitated because the operator does not need to incur the trouble of judging from his own experience numerous therapeutic conditions to be set and imparting them one by one. Moreover, this construction can prevent the operator from setting erroneous therapeutic conditions. Depending on the morbid state of each patient, therefore, the apparatus is enabled to heat accurately and easily the site of lesion exclusively and meanwhile prevent the normal tissue in the proximity of the site of lesion from sustaining damage.

The other objects, features, and characteristics of this invention will be apparent from the following description and the preferred embodiments illustrated in the drawings annexed hereto.

BRIEF DESCRIPTION OF THE DRAWINGS

FIG. 13A is a cross section drawn on a plane perpendicular to the axial direction of the main body of the apparatus, i.e. a diagram for explaining an experiment of heating a phantom equaling the prostate gland in size, FIG. 13B is a cross section drawn on a plane including the axis of the main body of the apparatus, i.e. a diagram for explaining an experiment of heating a phantom equaling the prostate gland in size, FIG. 14 is a diagram showing the results of an experiment of measuring temperature distribution of a heated tissue, FIG. 15A–FIG. 15C are diagrams showing in type specimens the ranges of temperature increase exceeding +8° C. as determined based on the results of experiment of FIG. 14, FIG. 21 is a flow chart illustrating a method for setting specific therapeutic conditions, FIG. 22 is a cross section of a vital tissue.

DETAILED DESCRIPTION OF THE PREFERRED EMBODIMENTS

Preferred embodiments of this invention will be described below with reference to the accompanying drawings.

Figure 1:
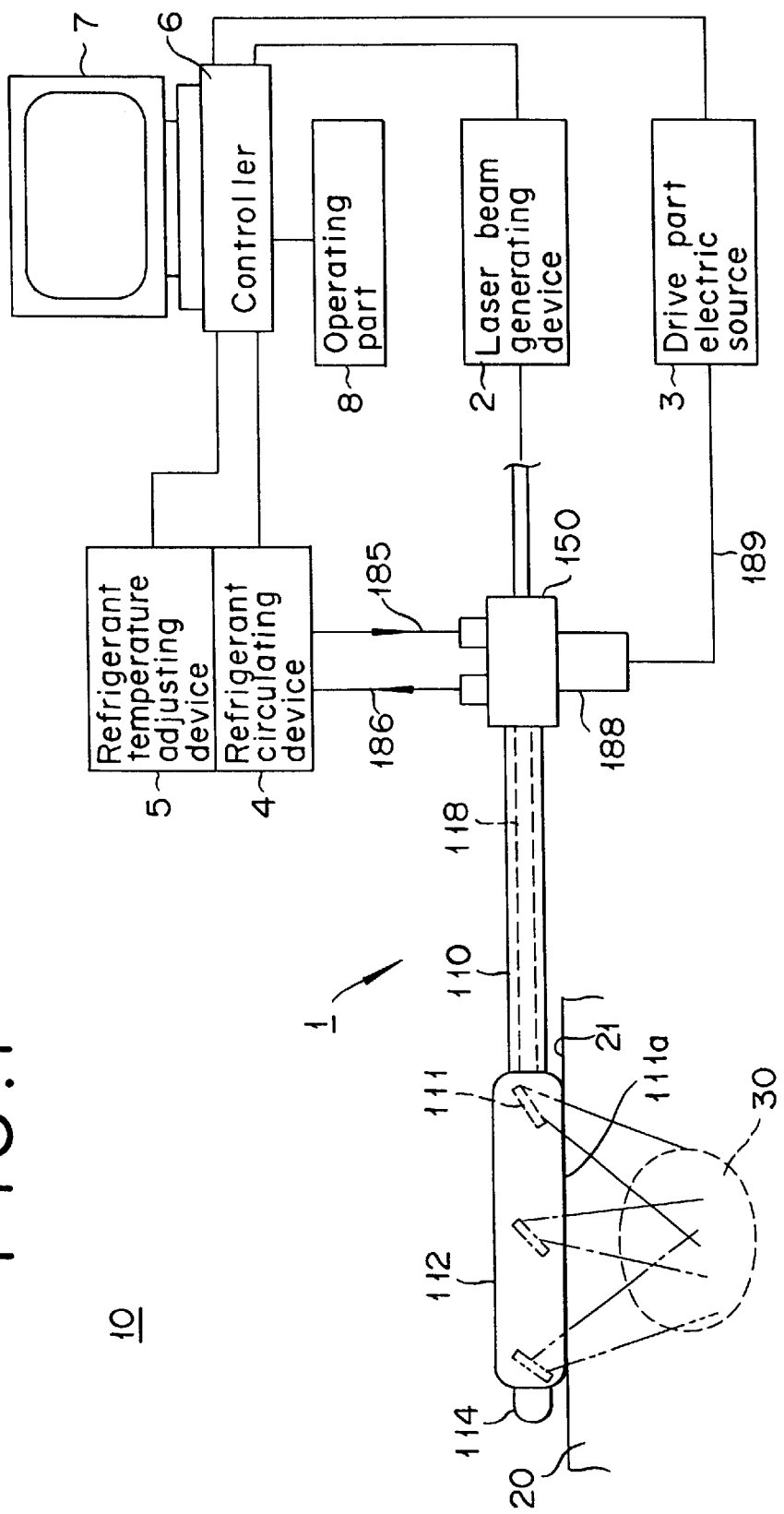
FIG. 1 is a system structure diagram of an apparatus for thermotherapy.
Figure 2:
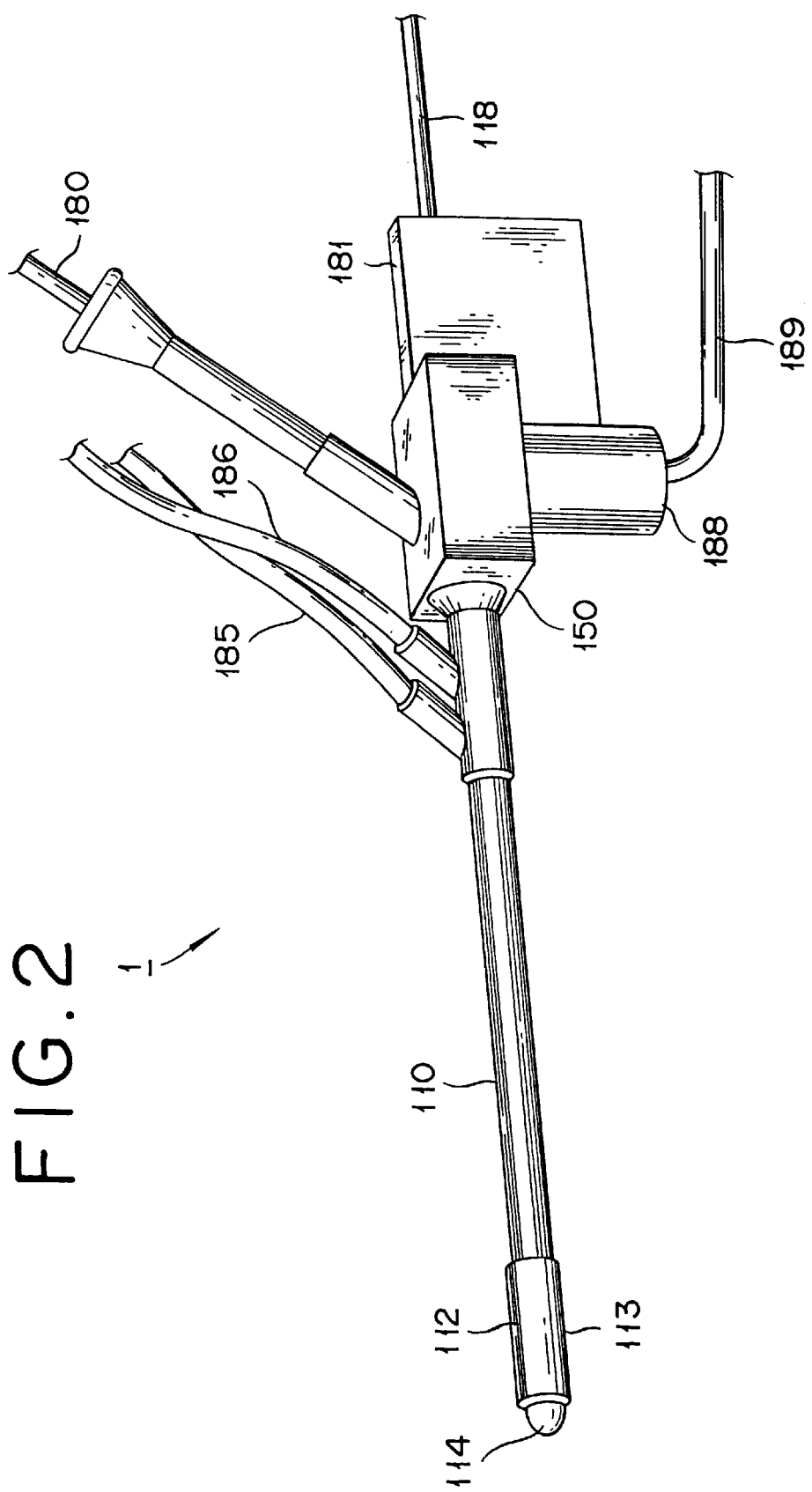
FIG. 2 is a perspective view of a device for emitting a laser beam.
Figure 3:
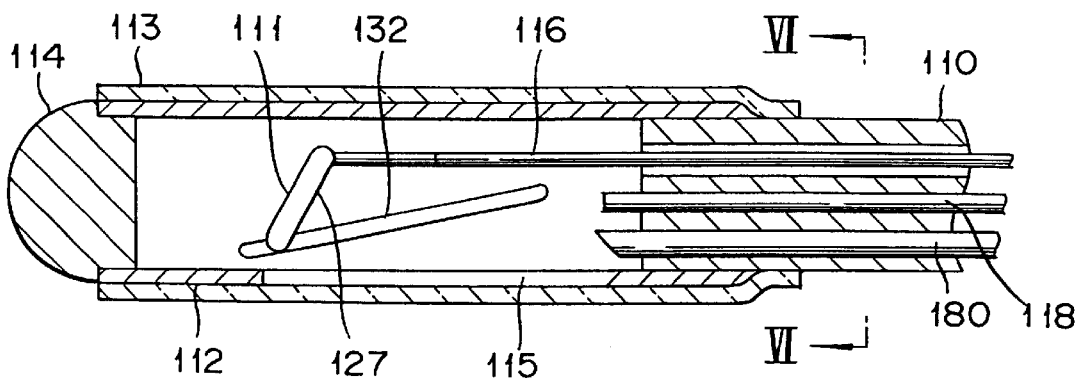
FIG. 3 is a cross section of the leading terminal part of the device for emitting a laser beam.

FIG. 1 is a system construction diagram of an apparatus for thermotherapy according to a first embodiment of the invention, FIG. 2 is a perspective view of a device for emitting a laser beam, and FIG. 3 is a cross section of the leading terminal part of the device for emitting a laser beam.

An apparatus for thermotherapy 10 illustrated in FIG. 1 is provided with a lateral emission type device 1 for emitting a laser beam which irradiates a vital tissue. This apparatus 10 for thermotherapy is intended to effect thermotherapy by inserting into a living body a main body 110 as a long and slender inserting part of the device 1 for emitting a laser beam and emitting a laser beam from an emitting part 111 disposed in the main body 110 toward a vital tissue 20. It is utilized for the therapy of benign prostatic hyperplasia and various ulcers including cancers.

The device 1 for emitting a laser beam, as illustrated in FIG. 2 and FIG. 3, is provided with the long and slender main body 110, the part 111 for emitting a laser beam to irradiate a site of lesion, and a housing 112 adapted to envelope the emitting part 111 and connected to the leading terminal part of the main body 110. one arm 116 is connected to the emitting part 111. The arm 116 supports the emitting part 111 inside the housing 112. The emitting part 111 is moved in the axial direction by moving the arm 116 in the axial direction of the main body 110. The emitting part 111 is formed on one side and is provided with a flat reflecting surface 127 for reflecting the laser beam.

The housing 112 is formed of a rigid tubular body containing a window part 115 for emitting the laser beam and is covered with a covering member 113 pervious to the laser beam. The housing 112 is possessed of an inner wall which is provided with a pair of grooves 132 for altering the angle of emission of the emitting part 111. The grooves 132 function as a guide for the emitting part 111 and are disposed opposite each other across the emitting part 111 and are laid not parallel to the axial direction of the main body 110, namely obliquely to the axial direction of the main body 110. Incidentally, the leading terminal part of the housing 112 is sealed with a cap 114.

An optical fiber 118 is disposed inside the main body 110 so as to guide the laser beam. The optical fiber 118 is an energy transmitting member. The optical fiber 118 is optionally provided at the leading terminal thereof with a leading terminal lens (not shown). This leading terminal lens is an optical element for converting the laser beam into collimating rays. The optical fiber 118 transmits the laser beam generated by a laser beam generating device 2. A buffer device 181 accommodates the optical fiber forming a loop and absorbs the motion of the optical fiber.

The laser beam emitting device 1 is further provided with a freely detachable oblique view type endoscope 180. The endoscope 180 is inserted from the basal terminal part through the leading terminal part of the laser beam emitting device 1. It is, therefore, capable of observing the surface layer irradiated by laser beam, the positioning of the housing based on the observation with the endoscope, and visually confirming the position for irradiation by the laser beam.

Figure 4:
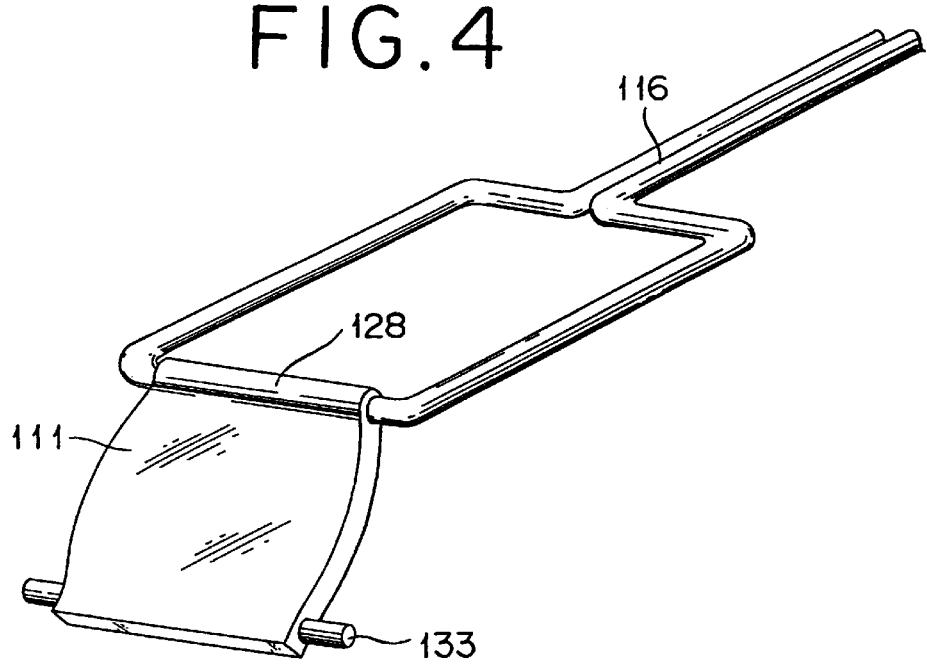
FIG. 4 is a perspective view for explaining the construction of an emitting part and an arm of the device for emitting a laser beam.

FIG. 4 is a perspective view for explaining the construction of an emitting part and an arm of the laser beam emitting device.

The arm 116 does not prevent the laser beam from impinging on the surface of the emitting part 111 because it is separated inside the housing 112 into two laterally opposed branches which serve the purpose of supporting the emitting part 111. The emitting part 111 is provided on one side thereof with a supporting part 128 and on the other side thereof with a pair of projections 133. The supporting part 128 is rotatably mounted on the arm 116 and enabled to correspond to an alteration in the angle of irradiation of the emitting part 111. The projections 133 fit into the grooves 132 disposed on the inner wall of the housing 112. The arm 116 is connected to a drive unit 150 disposed in the basal terminal part of the laser beam emitting device 1. To the drive unit 150 is connected a motor 188 which has electric power supplied from a power source 3 for the drive part through the medium of a cable 189. The drive unit 150 reciprocates the emitting part 111 in the axial direction of the main body 110. As a result, the emitting part 111 has an angle of inclination that changes with the position of the emitting part in the axial direction, based on the interlock between the arm 116 and the grooves 132.

Figure 5:
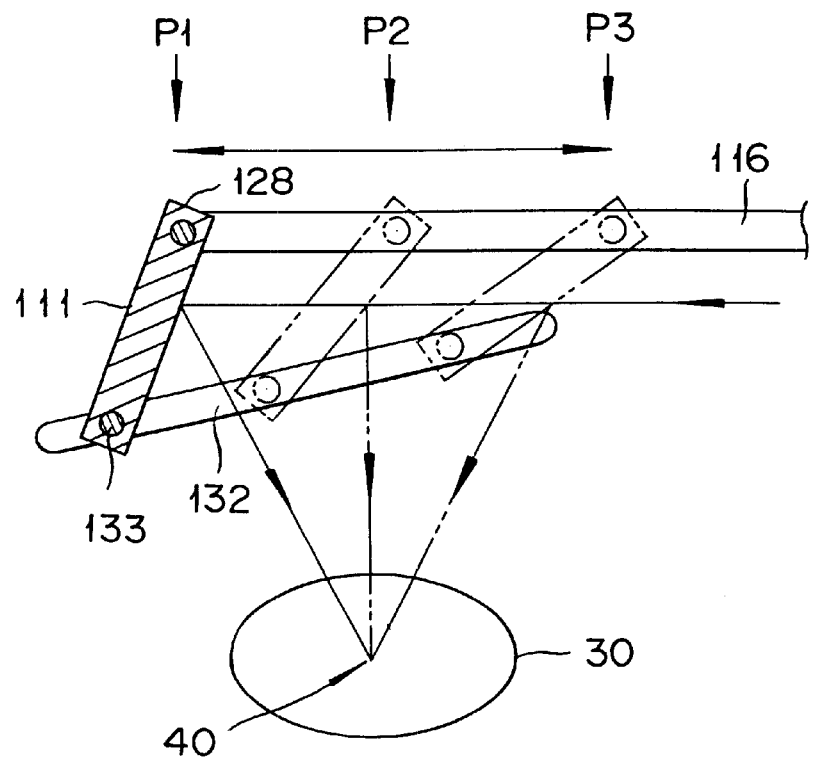
FIG. 5 is a diagram for explaining the relation between the movement of the emitting part and the direction of emission of an energy.

FIG. 5 is a diagram for explaining the relation between the motion of the emitting part and the direction of emission of energy.

As illustrated in FIG. 5, the distance between the arm 116 and the grooves 132 which are not parallel is shorter at a position P2 than at a position P1. When the supporting part 128 of the emitting part 111 moves from the position P1 to the position P2, therefore, the projections 133 of the emitting part 111 slide along the grooves 132 to adjust the angle of inclination of the emitting part 111. Specifically, the angle of inclination of the emitting part 111 relative to the axis of the main body 110 decreases. By the same token, when the supporting part 128 of the emitting part 111 moves from the position P2 to a position P3, the angle of inclination of the emitting part 111 relative to the axis of the main body 110 further decreases. The laser beam which is reflected by the emitting part 111 at the positions P1 through P3 is converged to a site of lesion, specifically a beam cross point 40.

That is, the laser beam is continuously projected to the beam cross point 40 exclusively and is intermittently projected to the other vital tissue such as the surface layer. The beam cross point 40, therefore, is heated to a prescribed temperature by the projected laser beam. The other vital tissue such as the surface layer is hardly heated because the duration of its exposure to the laser beam is short and the amount of heat generated is small.

The laser beam, to be projected from the emitting part 111 may be diverging rays, preferably collimating rays, or converging rays.

When the laser beam projected from the emitting part 111 is in the form of collimating rays or converging rays, the energy density of the laser beam at the beam cross point 40 and in the proximity thereof can be enhanced because the laser beam enjoys a fine property of convergence. In other words, when the energy density of the laser beam formed of collimating rays or converging rays and the energy density of the laser beam formed of diverging rays are equally set on the beam cross point 40, the former energy density is lower than the latter energy density in the surface layer. The laser beam formed of collimating rays or converging rays, therefore, prevents the surface layer from damage more infallibly than the laser beam formed of diverging rays.

When the laser beam projected from the emitting part 111 is formed of converging rays, the apparatus is preferably constructed that the beam cross point 40 coincides with the focal position of the laser beam, namely the position at which the plane of the laser beam perpendicular to the axis thereof assumes the smallest possible area. In this case, since the focal point of the laser beam overlaps the beam cross point 40, the energy density of the laser beam can be further enhanced at the beam cross point 40 and the proximity thereof.

For the purpose of enabling the laser beam projected from the emitting part 111 to assume the form of converging rays, an optical system capable of converting a laser beam into converging rays is provided halfway along the length of the light path for the laser beam. In the laser beam emitting device 1, a lens (not shown) forming the optical system is disposed at the leading terminal part of the optical fiber 118. Incidentally, by forming the reflecting surface 127 of the emitting part 111 with a concave mirror, the emitting part 111 can function concurrently as an optical system.

Practically, the portion of tissue which is heated to the highest temperature is located closer to the surface layer than the beam cross point 40 because the vital tissue exerts an influence on the absorption and scattering of the laser beam. The depth and the temperature of a portion to be heated to the highest temperature can be adjusted of suitably cooling the surface layer, changing the power of a laser beam, etc. Thus, the depth and the size of the target site 30 can be controlled without varying a position of the beam cross point 40.

Incidentally, the laser beam emitting device 1 is made applicable to a site of lesion with a complicated shape by properly designing the relation between the arm 116 parallel to the axial direction of the main body 110 and the grooves 132 not parallel thereto, and the shape of the grooves 132. The grooves 132, for example, do not need to be in a rectilinear shape but may be in a curved shape when occasion demands.

Figure 6:
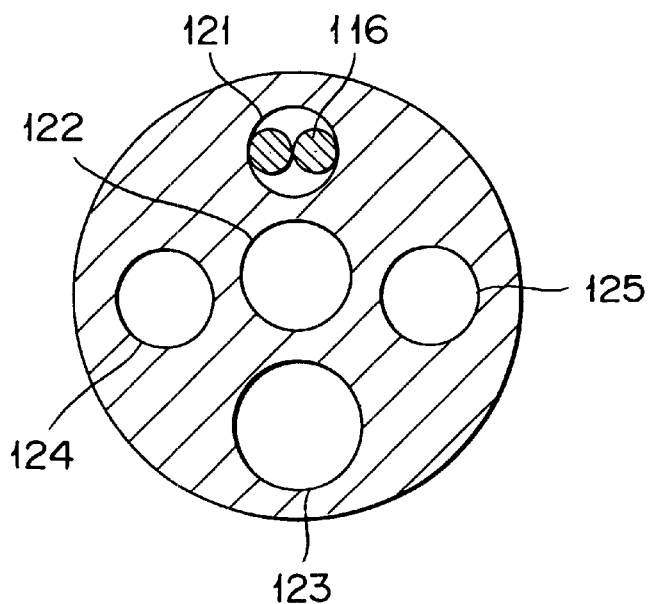
FIG. 6 is a cross section taken through FIG. 3 along the line VI—VI.

FIG. 6 is a cross section taken through FIG. 3 along the line VI—VI.

As illustrated in FIG. 6, the main body 110 is provided with a working lumen 121 which has the arm 116 inserted slidingly therein. The working lumen 121 is formed parallel to the axial line of the main body 110. The main body 110 is further provided with a lumen 122 for use by the optical fiber 118, a lumen 123 for use by the endoscope 180, a lumen 124 for use in the injection of the refrigerant, and a lumen 125 for use in the discharge of the refrigerant. The refrigerant is for repressing the heat generated by the laser beam in the housing 112 and for cooling the surface layer of the vital tissue contiguous to the housing 112 as well. The lumens 124 and 125 are connected via respective connectors (not shown) to tubes 185 and 186 (FIG. 1 and FIG. 2 refer) for injecting and discharging the refrigerant respectively from and to a refrigerant circulating device 4. The refrigerant circulating device 4 is furnished with a refrigerant temperature adjusting device 5 which is capable of adjusting the temperature of the refrigerant to be circulated. For the purpose of preventing the refrigerant from flowing back toward the basal terminal part, the rumens 121, 122, and 123 are each preferred to be provided with a check valve. Optionally, the working lumens 121 and 122 may be concurrently used for injecting and discharging the refrigerant. The refrigerant is preferred to be a sterilized water or a physiological saline solution. The reason for this preference is that when this refrigerant happens to leak by some cause or other in the intracorporeal system, the leakage has a small influence on the living body.

Figure 7:
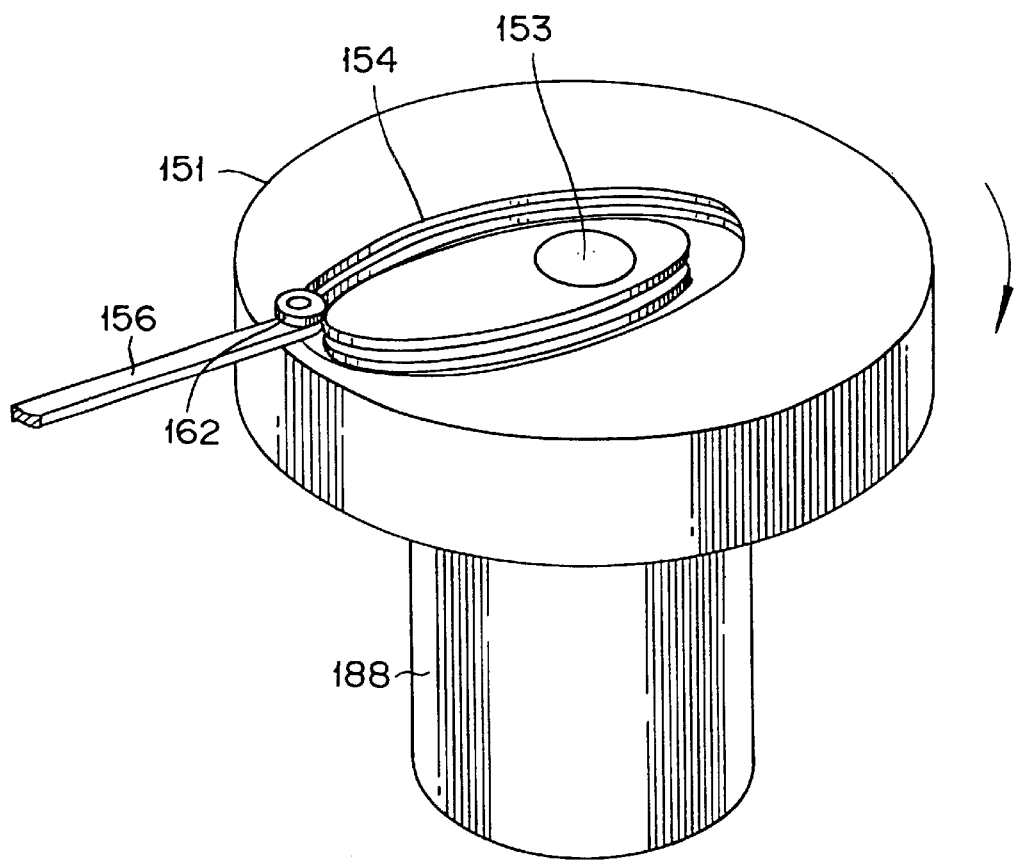
FIG. 7 is a perspective view for explaining the construction of a drive unit of the device for emitting a laser beam.

FIG. 7 is a perspective view for explaining the construction of a drive unit of the laser beam emitting device.

As illustrated in FIG. 7, the drive unit 150 for reciprocating the emitting part 111 is provided with a grooved cam 151. The grooved cam 151 is furnished with an elliptic groove 154. A rotating shaft 153 of the grooved cam 151 is connected to the shaft of the motor 188 and does not coincide with the center of the groove 154. The drive unit 150 is further provided with a cam follower 162 disposed at the basal terminal of a rod 156 which is connected to the basal terminal of the arm 116. The cam follower 162 is fitted slidably into the groove 154.

The grooved cam 151 is driven by the motor 188 and is rotated about the rotating shaft 153 as the center. Meanwhile the cam follower 162 is not rotated, but moved slidingly along the groove 154. Since the rotating shaft 153 is eccentric from the groove 154, the rod 156 and the arm 116 connected to the rod 156 produce a reciprocating motion, namely repeat a translating motion.

Figure 8:
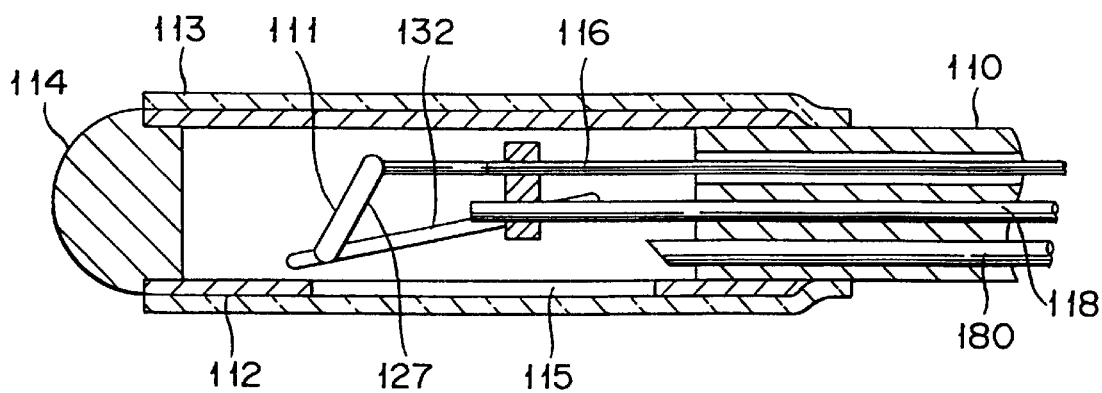
FIG. 8 is a diagram illustrating an example of fixing the proximity of the leading terminal of an optical fiber to the arm.

FIG. 8 is a diagram illustrating an example of fixing the proximity of the leading terminal of the optical fiber 118 to the arm 116. In this construction, since the optical fiber 118 and the arm 116 are jointly reciprocated, the leading terminal of the optical fiber 118 irradiated with the laser beam is constantly kept at a fixed distance relative to the reflecting surface 127. In this case, the optical fiber 118 does not need to be provided at the leading terminal thereof with an optical element for converging or collimating light. When diverging rays are used, the numerical aperture is not more than 0.4, preferably not more than 0.3.

Figure 9:
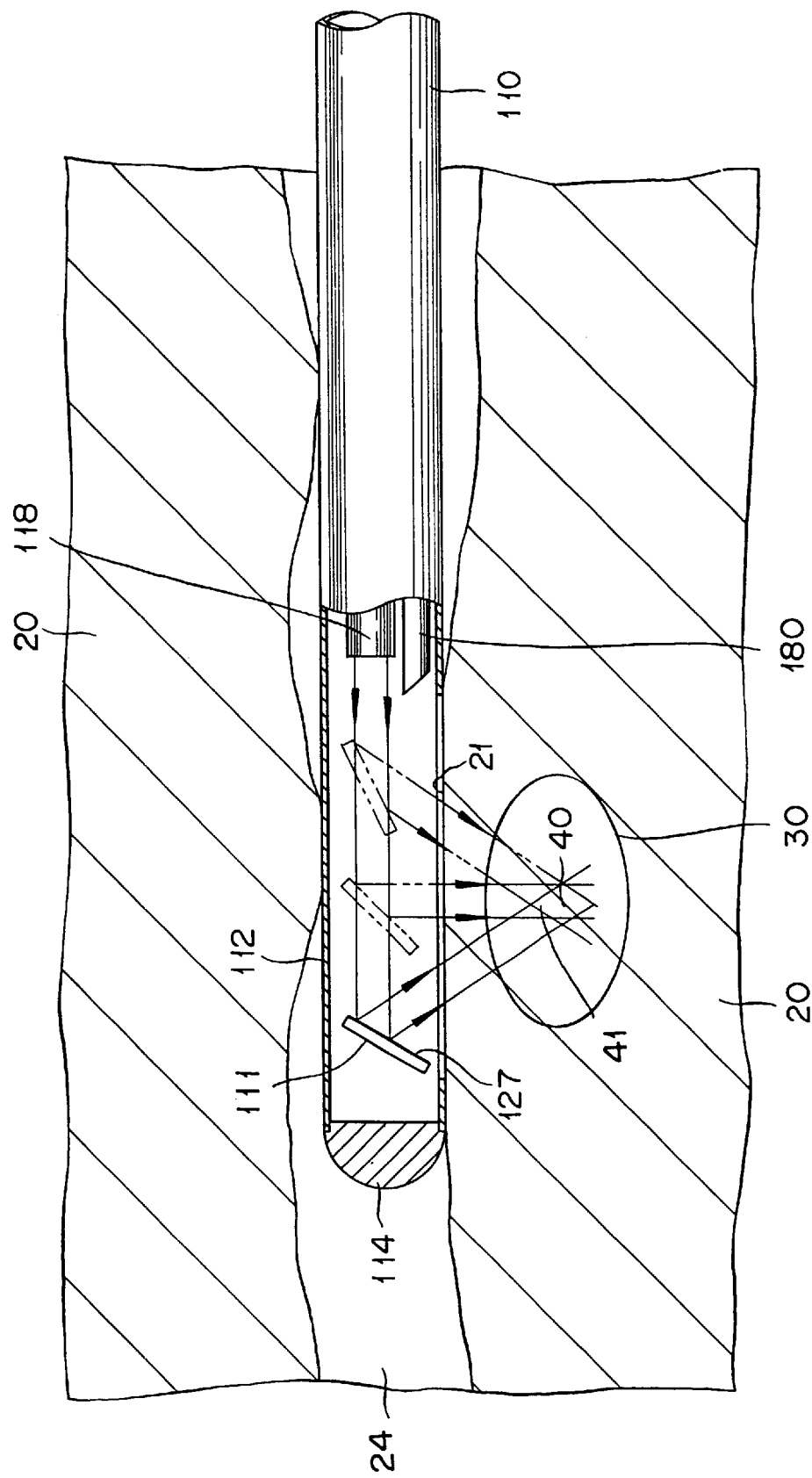
FIG. 9 is a cross section for explaining an example of the use of-the device for emitting a laser beam.

FIG. 9 is a cross section for explaining an example of using the laser beam emitting device.

First, the leading terminal part of the main body 110 is inserted into a vital lumen 24 until the housing 112 accommodating the emitting part 111 tightly contacts the site of lesion, i.e. the surface layer 21 in the proximity of the target site 30 which is the target site of heating. At this time, it is preferred that the position of the housing 112 be directly confirmed with the endoscope 180. Incidentally, the position of the beam crosspoint 40 relative to the longitudinal direction of the main body 110 is adjusted by moving the whole of the laser beam emitting device 1 in the longitudinal direction of the main body 110. The position of the beam cross point 40 relative to the circumferential direction of the main body 110 is adjusted by manually rotating the whole of the laser beam emitting device 1.

Then, the laser beam generating device 2 is actuated and, at the same time, the motor 188 is set rotating. The laser beam consequently generated is introduced via a connector not shown into the laser beam emitting device 1.

The laser beam is further advanced through the optical fiber 118, guided from the basal terminal part to the leading terminal part of the laser beam emitting device 1, reflected by the reflecting surface 127 of the emitting part 111 inside the housing 112, and projected to the beam cross point 40. The emitting part 111 is reciprocated in the axial direction, with the angle of emission altered in a cycle of 0.1–10 Hz, preferably 1–6 Hz. The light path for the laser beam is continuously altered but the component beams of the laser never fail to cross at the beam cross point 40.

Consequently, the beam cross point 40 in the vital tissue 20 and the proximal areas are heated to an expected temperature by the laser beam impinging thereon. However, the temperature of a portion slightly nearer to the surface layer than the beam cross point 40 is generally to be heated to the highest temperature based on the absorption and scattering of the laser beam in the vital tissue 20. In other words, the point to be heated to the highest temperature, i.e. the target point 41 is different from the beam cross point 40. The duration of the projection of the laser beam to the region on the upper side in the bearings of FIG. 9 (namely above the target site 30 such as, for example the surface layer 21 of the vital tissue 20) is short, and consequently the amount of heat generated is small. Similarly, the duration of the projection of the laser beam to the region on the lower side in the bearings of FIG. 9, namely below the target site 30, is short and consequently the amount of heat generated is small. That is, since the laser beam from the continuously moved position of emission is converged to the beam cross point 40, the neighboring site (normal tissue) parted from the target site 30 is maintained at a comparatively low temperature and is protected from the influence of the laser beam. Since the region other than the target site 30 is prevented from sustaining damage or to sustain damage only sparingly, the laser beam emitting device 1 provides high safety for a patient. Even when the target site 30 is very deep within the vital tissue, the laser beam emitting device 1 is at an advantage in preventing the surface layer from sustaining damage. The heating of an expected region can be also accomplished by means of changing the location of the beam cross point 40 and then irradiating the region with a laser beam.

The laser beam to be used does not need to be particularly discriminated so long as it possesses an ability to reach a great depth in the living body. The wavelength of the laser beam is preferred to be in the approximate range of 750–1300 nm or 1600–1800 nm. In this range of wavelength, the laser beam is possessed of an outstanding ability to reach a great depth in the living body. That is, since the surface layer of the vital tissue absorbs only a small portion of the energy of the projected laser beam, the laser beam is projected more effectively to the target site 30 which is located at a great depth in the vital tissue.

For example, the gaseous laser such as the He—Ne laser, the solid laser such as the ND-YAG laser, and the semiconductor laser such as the GaAlAs laser can be effectively applied to the laser beam generating device 2 which generates a laser beam having a wavelength in the range mentioned above.

The diameter of the inserting part of the laser beam emitting device 1, namely the outside diameter of the main body 110, does not need to be particularly limited so long as the inserting part is capable of being inserted into a given vital lumen 24. The outside diameter of the main body 110, however, is properly in the approximate range of 2–20 mm, preferably 3–8 mm.

As concrete examples of the material for forming the main body 110, polyolefins such as polyethylene and polypropylene, ethylene-vinyl acetate copolymer (EVA), polyvinyl chloride, polyesters such as polyethylene terephthalate and polybutylene terephthalate, polyamides, polyurethane, polystyrene, polycarbonate and fluorine resin, polymer alloys containing any of the materials mentioned above or a combination of two or more such materials may be cited. Metallic materials such as stainless steel, titanium and titanium alloy may also be cited as other examples.

A lubricating coating layer incorporating therein a material such as silicon or fluorine resin which is endowed with low property of friction or a hydrophilic macromolecular material may be formed on the surface of the main body 110. In this case, since the coating layer allays the surface friction of the main body 110, the main body 110 is smoothly inserted into the body cavity. optionally, the lubricating coating layer may be formed on the surface of a disposable sheath which is separately prepared and used for covering the main body 110. In this case, the harmful effect produced by repeated use, namely the loss of lubricity due to the separation of the lubricating coating layer, can be prevented.

As concrete examples of the hydrophilic macromolecular material to be advantageously used for the lubricating coating layer, carboxymethyl cellulose, polysaccharides, polyvinyl alcohol, polyethylene oxide, sodium polyacrylate, methyl vinyl ether-maleic anhydride copolymer, and water-soluble polyamide may be cited. Among other materials mentioned above, the methyl vinyl ether-maleic anhydride copolymer proves to be particularly favorable.

When the laser beam emitting device having its main body coated with a hydrophilic macromolecular material is put to use, the main body is immersed, for example, in a physiological saline solution. Consequently, the surface layer of the main body is wetted and the device is endowed with lubricity. That is, when the device is possessed of the surface layer containing the hydrophilic macromolecular material, the frictional resistance between the vital tissue and the device is lowered. The lowered frictional resistance alleviates the burden on the patient and enhances the safety as well. For example, the insertion of the device into the body cavity, the extraction thereof from the body cavity, the movement and the rotation of the device inside the body cavity are executed smoothly.

The housing 112 is preferably formed of a material such as, for example, quartz glass, acrylic resin, polystyrene, polycarbonate, polyethylene, polypropylene, vinylidene chloride, or polyester which is possessed of outstanding perviousness to the laser beam. The housing 112 does not need to be formed wholly of such material excelling in perviousness to the laser beam. For example, it is possible to form only the window part for emitting the laser beam of the material laser-pervious with the remainder formed of the same material as the main body 110. When the window part for emitting the laser beam is formed of the material which is pervious to the laser beam, the laser beam can be efficiently projected. It is also allowable to form the window part for emitting the laser beam with an opening and form the covering member 113 for covering the housing 112 with the laser-pervious material mentioned above.

The energy transmitting member does not need to be limited to the optical fiber but may be formed of a material such as, for example, a rod lens which is capable of guiding the laser beam. The emitting part does not need to be limited to a plate possessed of a smooth reflecting surface but may be formed of a prism or a wedge plate, for example.

The laser beam generating device 2, the drive part electric source 3, the refrigerant circulating device 4, and the refrigerant temperature adjusting device 5 mentioned above are connected respectively to a controller 6 as a control means as illustrated in FIG. 1. Further, to the controller 6 are connected an operating part 8 as an input means, a monitor 7 for displaying input information and results of computation, and other input/output devices not shown. The controller 6 manages the overall control of the apparatus 10 for thermotherapy.

The apparatus 10 for thermotherapy in the present mode of embodiment is so constructed as to set therapeutic conditions for effecting the thermotherapy of the prostate gland based on the input information concerning the diagnostic data of the prostate gland, particularly the input information containing the data for specifying the size of the prostate gland.

Figure 10:
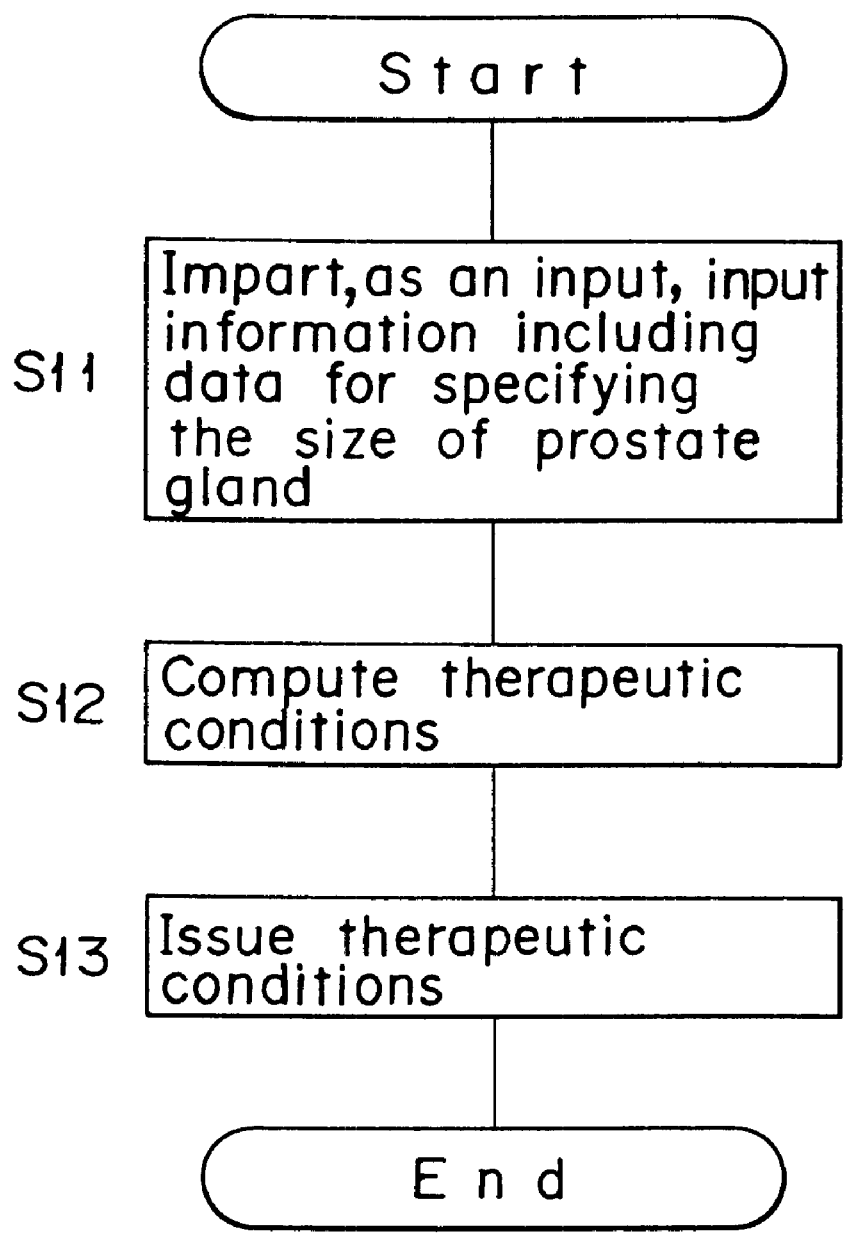
FIG. 10 is a flow chart illustrating a method for setting therapeutic conditions of an apparatus for thermotherapy according to a first embodiment.

FIG. 10 is a flow chart illustrating a method for setting the therapeutic conditions.

The physician, prior to use of the apparatus for thermotherapy, examines the prostate gland of a patient by way of diagnosis. The shape and the size of the prostate gland are diagnostically determined, for example, by the palpation (indirectly by the insertion of a finger into the rectum), the ultrasonography, the magnetic resonance imaging method (MRI), the computed tomography using X ray or magnetic resonance (CT), or the biopsy. Then, the hardness or the tissue density of the prostate gland is diagnostically determined by the palpation (indirectly by the insertion of a finger into the rectum), the magnetic resonance imaging method, the computed tomography using X ray or magnetic resonance, or the biopsy. The flow volume of blood in the prostate gland is diagnostically determined by the per rectum ultrasound Doppler effect.

The operator secures input information including the data for specifying the size of the prostate gland from the tissue of prostate gland diagnostically determined and imparts the input information to the apparatus via the operating part 8 (S11). The expression "the data for specifying the size of the prostate gland" as used herein refers to the diagnostic data useful for discerning the size of the prostate gland. It embraces the diameter of the prostate gland, and the volume and the weight of the prostate gland, for example. The other items of the input information include the tissue density of the prostate gland and the flow volume of blood within the prostate gland, for example. The controller 6 may be so constructed as to read the input information including the data for specifying the size of the prostate gland from the diagnostic data of a given patient stored in a memory not shown. The input means does not need to be limited to the operating part 8. The controller 6, when necessary, may be provided with a connecting part which, when connected to such an external device as a prostate gland diagnosing device not shown or a computer memorizing patient information not shown, is enabled to obtain as an input from the external device the information including the diagnostic data of the prostate gland. When this connecting part is used during the course of diagnosis or at the operator's own discretion, the information containing the diagnostic data of the prostate gland is transferred to the controller 6, with the result that the therapeutic conditions will be automatically set, the trouble of imparting the information with the aid of the operating part 8 will be avoided, and the possibility of entailing erroneous impartation through the operating part 8 will be precluded.

The controller 6 computes the therapeutic conditions necessary for thermotherapy based on the input information introduced into the operating part 8 (S12). As concrete examples of the therapeutic conditions for the apparatus 10 for thermotherapy, the power of the laser beam, the duration of emission of the laser beam, the temperature of the refrigerant forwarded to the main body 110, the flow volume of the refrigerant sent to the main body 110, and the speed of movement of the laser beam emitting part may be cited. The apparatus 10 for thermotherapy automatically computes one or more of these therapeutic conditions. The method adopted for this computation of the therapeutic conditions consists in substituting the input information introduced into the operating part 8 for the relevant terms of the relational expressions obtained in advance empirically, for example. Alternatively, the method which makes use of a function table empirically obtained in advance may be adopted. As a general trend, the power of the laser beam is set in a higher direction, the duration of emission of the laser beam in a longer direction, the temperature of the refrigerant in a lower direction, the flow volume of the refrigerant in a larger direction, and the speed of movement of the laser beam emitting part in a faster direction in proportion as the size of the prostate gland increases or the flow volume of the blood in the prostate gland increases. Then, when the heat source is a laser beam, the power of the laser beam is set in a higher direction, the duration of emission of the laser beam in a longer direction, the temperature of the refrigerant in a lower direction, the flow volume of the refrigerant in a larger direction, and the speed of movement of the laser beam emitting part in a faster direction in proportion as the tissue density of the prostate gland increases.

Then, the controller 6 issues the therapeutic conditions which have been found by the automatic computation (S13). Specifically, the controller 6 emits control signals respectively to the laser beam generating device 2, the drive part electric source 3, the refrigerant circulating device 4, and the refrigerant temperature adjusting device 5, depending on the therapeutic conditions which have been obtained. The therapeutic conditions thus obtained are displayed on the monitor 7 together with the input information introduced into the operating part B. Thus, the controller 6 automatically sets the therapeutic conditions for effecting thermotherapy, based on the input information introduced into the operating part 8. As the therapeutic conditions which are not automatically set on the basis of the input information, such numerical values as are generally applicable to the thermotherapy are adopted.

The controller 6, when necessary, may be so adapted that it will first display the therapeutic conditions found by the automatic computation and/or other therapeutic conditions on the monitor 7 and, after the operator has confirmed the contents of the display and then depressed a prescribed switch on the operating part 8, will emit a control signal to the laser beam generating device 2, for example. Further, the controller 6 may be so adapted as to enable manual impartation of fine adjustment of a certain degree or other to the therapeutic conditions found by the automatic computation and/or other therapeutic conditions.

The apparatus 10 for thermotherapy, as described above, only requires introduction of the input information including the data for specifying the size of the prostate gland for the purpose of automatically setting proper therapeutic conditions. The operator, therefore, finds the operation of input easy because he is no longer required to judge from his own experience such numerous therapeutic conditions as are to be set and impart such therapeutic conditions to the apparatus. The apparatus 10 further is capable of preventing erroneous therapeutic conditions from being set. It is, therefore, capable of avoiding infliction of damage to the normal tissue in the proximity of the site of lesion and ensuring accurate and easy application of heat exclusively to the site of lesion.

Figure 11:
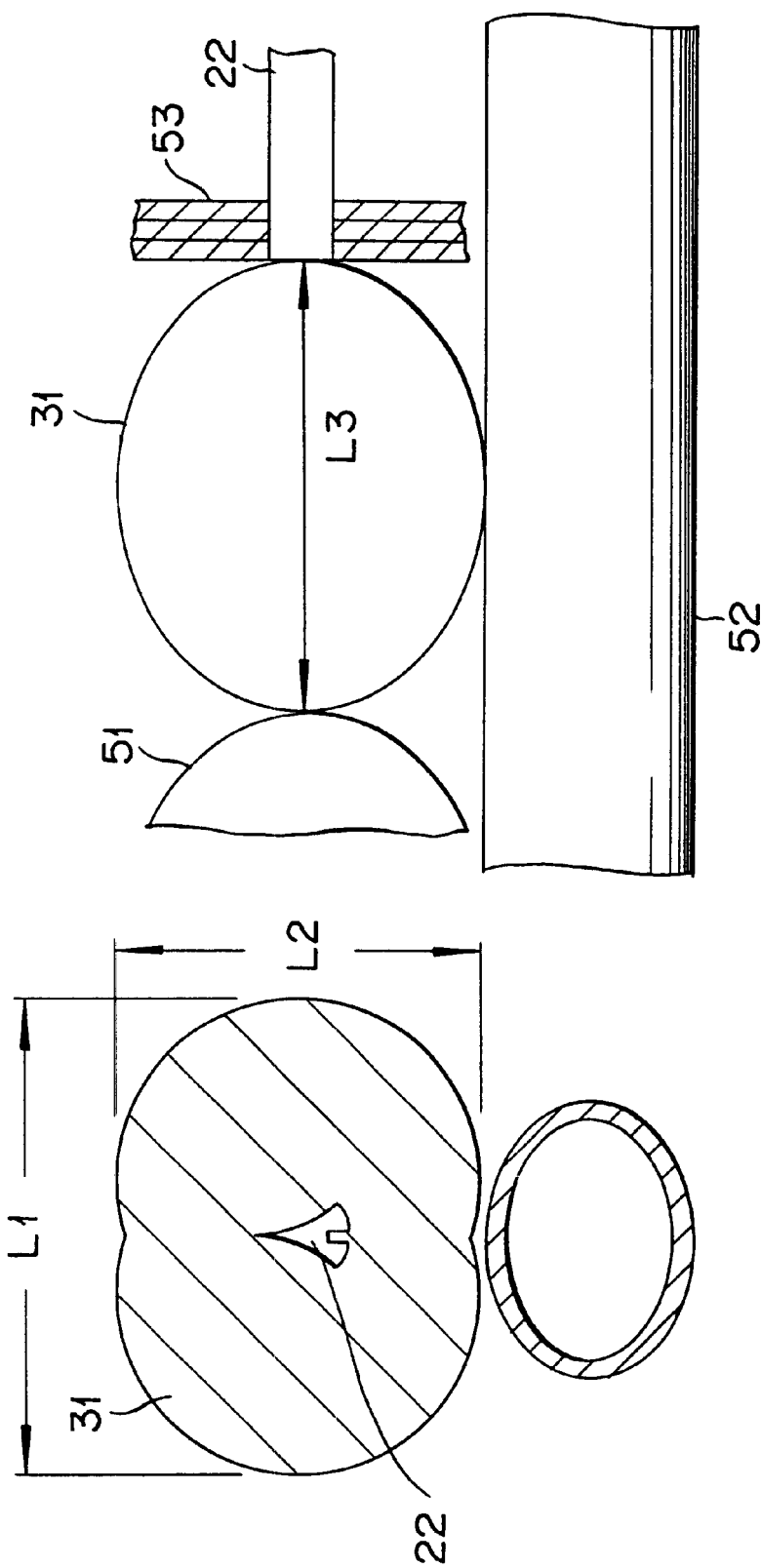
FIG. 11A is a cross section of a vital tissue in the proximity of the prostate gland drawn on a plane perpendicular to the urethra.
FIG. 11B is a diagram illustrating FIG. 11A as viewed from the lateral side.
Figure 12:
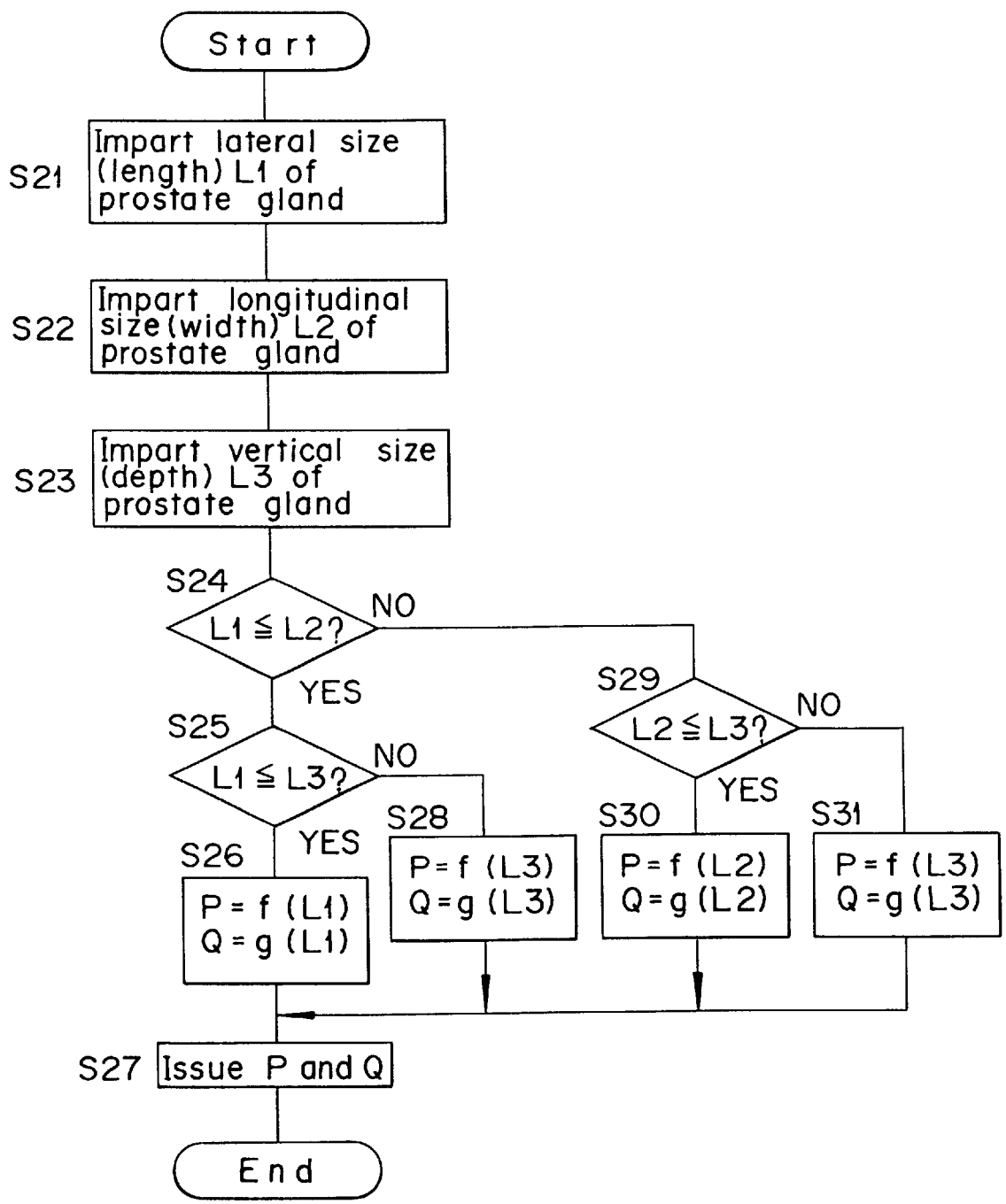
FIG. 12 is a flow chart illustrating a method for setting specific therapeutic conditions.

FIG. 11A is a cross section of the vital issue in the proximity of the prostate gland as taken in a plane perpendicular to the urethra, FIG. 11B is a view of FIG. 11A as seen from the lateral side thereof, and FIG. 12 is a flow chart illustrating a method for setting specific therapeutic conditions.

The method for setting therapeutic conditions illustrated in FIG. 12 is more specific than the method for setting therapeutic conditions illustrated in FIG. 10 in respect that the input information introduced into the operating part 8 comprises diameters of the prostate gland in the three axial directions defining a space. In the following description, therefore, those parts which overlap those given above will be partly omitted.

A prostate gland 31, as illustrated in FIG. 11A and FIG. 11B, is so positioned as to encircle the urethra 22 which communicates with a bladder 51. A rectum 52 passes near the prostate gland 31. The reference numeral 53 appearing in the diagram denotes a sphincter muscle of urethra.

The three axial directions that define space preferably intersect each other orthogonally. The diameters of the prostate gland respectively in the three axial directions as involved herein are diameters L1 and L2 in two orthogonally crossing axial directions in a plane perpendicular to the urethra 22 penetrating the prostate gland 31 and a diameter L3 in an axial direction parallel to the urethra 22. Incidentally, as the data for specifying the size of the prostate gland, one or more of the diameters of the prostate gland-respectively in the three axial directions mentioned above may be adopted.

The physician, prior to the use of the apparatus for thermotherapy, diagnostically determines the site of lesion of a given patient. From the tissue of the prostate gland thus comprehended diagnostically, the physician delivers the diameters L1 (mm), L2 (mm), and L3 (mm) of the prostate gland respectively in the three axial directions defining space to the apparatus via the operating part 8 (S21, S22, S23).

The controller 6 first decides the minimum diameter $L_{min}$ from among the diameters L1, L2, L3 of the prostate gland introduced into the operating part 8 (S24, S25, S29) and, based on this minimum diameter $L_{min}$, computes automatically the power P of the laser beam and the flow volume Q of the refrigerant forwarded to the main body 110, which are therapeutic conditions for effecting thermotherapy (S26, S28, S30, S31). For this computation of the therapeutic conditions, the method which comprises finding the power P of the laser beam and the flow volume Q of the refrigerant forwarded to the main body 110 by substituting the diameters L1, L2, L3 of the prostate gland introduced into the operating part 8 for the relevant terms of the relational expressions found in advance empirically is adopted.

Next, the controller 6 issues the therapeutic conditions which have been found by the automatic computation (S27). To be specific, the controller 6 delivers control signals to the laser beam generating device 2 and the refrigerant circulating device 4, depending on the therapeutic conditions to be consequently obtained. Further, the therapeutic conditions so obtained are displayed on the monitor 7 together with the input information introduced into the operating part 8. Thus, the controller 6 automatically sets the therapeutic conditions necessary for thermotherapy, based on the diameters L1, L2, L3 of the prostate gland introduced into the operating part 8. As the therapeutic conditions which are not automatically set on the bas is of the input information, such numerical values as are generally applicable to the thermotherapy are adopted. The controller 6, depending on these therapeutic conditions, emits control signals to the drive part electric source 3 and the refrigerant temperature adjusting device 5.

According to the method for setting the therapeutic conditions illustrated in FIG. 12, by simply imparting the diameters L1, L2, L3 of the prostate gland depending on the morbid state of each patient, the therapeutic conditions for effectively heating exclusively the site of lesion can be set accurately and very easily without committing any error while the normal tissue in the proximity of the site of lesion is prevented from sustaining damage. Further, since the therapeutic conditions for performing the thermotherapy are set based on the minimum diameter $L_{min}$ among other diameters L1, L2, L3 of the prostate gland, the possibility of accidentally heating the normal tissue outside the prostate gland can be avoided and the proper thermotherapy can be fulfilled with high reliability.

The method for setting the therapeutic conditions, as illustrated in FIG. 12, has limited the therapeutic conditions to be automatically set to the power P of the laser beam and the flow volume of the refrigerant to be forwarded to the main body 110. This invention does not need to adhere to this particular limitation. For example, it is made possible to set automatically the duration of emission of the laser beam, the temperature of the refrigerant to be sent to the main body 110, and the speed of movement of the laser beam emitting part by simply imparting as an input the data for specifying the size of the prostate gland.

When the diameter of the prostate gland imparted as an input to the operating part 8 is smaller than the minimum characteristic value which is set in advance, the control for terminating the thermotherapy may be incorporated in the therapeutic conditions. By so doing, the accidental application of heat to the normal prostate gland can be conditions.

Object for heating: Chicken (as phantom)
Laser beam: Wavelength 810 nm, continuous wave, beam diameter on the surface of tissue 4 mm, numerical aperture NA=0.26
Ambient Temperature: Room temperature 22° C.
Duration of heating (duration of emission of laser beam): 15 minutes Temperature of refrigerant: 22° C.
Speed of movement of laser beam emitting part: 3 reciprocations/second
Length of movement of laser beam emitting part: 20 mm
Distance from the emitting terminal to the beam cross point: 15 mm
Temperature set for heating: Temperature increase at a depth from the urethra in the range of 4 mm to (minimum diameter $L_{min}/2-8$) mm not less than +8° C.

The relational expressions empirically obtained in advance to be used for finding the power P (W) of the laser beam and the flow volume Q (ml/min) of the refrigerant forwarded to the main body 110 from the minimum diameter the among other diameters L1 (mm), L2 (mm), and L3 (mm) in the three axial directions are as follows.

Where $46 \leq L_{min} \leq 52$;

$$P = A1 \cdot L_{min}^2 - B1 \cdot L_{min} + C1 \quad (1\text{-}1)$$

$$Q = A2 \cdot L_{min}^2 - B2 \cdot L_{min} + C2 \quad (1\text{-}2)$$

wherein
A1=0.0333, B1=3, and C1=76.07 and
A2=2.0833, B2=187.5, and C2=4267

Concerning FIG. 13, three experiments exist, i.e. Experiment 1: L1=48, L2=46, L3=51 ($L_{min}$=46), Experiment 2: L1=50, L2=52, L3=54 ($L_{min}$=50), and Experiment 3: L1=55, L2=53, L3=52 ($L_{min}$=52). In these experiments 1–3, by imparting the diameters L1 (mm), L2 (mm), and L3 (mm) in the three axial directions as an input into the operating part 8 of the apparatus 10 for thermotherapy, the power P (W) of the laser beam and the flow volume Q (mi/min) of the refrigerant to be forwarded to the main body 110 as the therapeutic conditions are respectively set as follows in accordance with the expressions (1-1) and (1-2).

The results, Experiment 1: P=8.5 and Q=50, Experiment 2: P=9.3 and Q=100, and Experiment 3: P=10.1 and Q=150, are obtained.

Under the therapeutic conditions set as described above, an object for heating was heated. and the temperature distribution in the object thus heated was measured to a depth of 20 mm from the surface of the object.

FIG. 14 is a diagram illustrating the results of the experiment of measuring the temperature distribution of the heated object and FIG. 15 is a diagram illustrating as a type specimen the range in which the temperature rise was found to be not less than +8° C. based on the results of experiment of FIG. 14. In FIG. 14, "$L_{min}$=46 mm" represents the result of measurement of temperature distribution in Experiment 1, "$L_{min}$=50 mm" represents the result of measurement of temperature distribution in Experiment 2, and "$L_{min}$=52 mm" represents the result of measurement of temperature distribution in Experiment 3. FIG. 15A corresponds to Experiment 1, FIG. 15B to Experiment 2, and FIG. 15C to Experiment 3.

By referring to FIG. 14 and FIG. 15A–FIG. 15C, it is noted that the present apparatus for thermotherapy is capable of accurately and easily heating as aimed at a depth from the urethra in the range 33 from 4 mm to (minimum diameter $L_{min}/2-8$) mm, with the temperature rise not less than +8° C. That is, it has been established that the temperature rise can be kept below +8° C. to a depth of 4 mm from the surface of the surface layer of the urethra and to a depth of 4 mm from the inner side of the spherical surface of the minimum diameter $L_{min}$.

The apparatus of this invention for thermotherapy is preferably applied to the thermotherapy of such diseases of the prostate gland as the prostatomegaly and the cancer of the prostate gland, wherein the interior of the prostate gland is exclusively heated to a predetermined temperature without heating the normal tissue of the urethra and the rectum existing in the proximity of the prostate gland to a level above the predetermined temperature.

The apparatus for thermotherapy in the embodiment described above, as explained above, have particularly cited the diameters L1, L2, and L3 in the three axial directions of the prostate gland 31 as the data for specifying the size of the prostate gland. This invention does not need to adhere to this limitation. It is allowable, as already described above, to adopt the volume and the weight of the prostate gland as the data far specifying the size of the prostate gland. It is also permissible to use the hardness or the tissue density of the prostate gland or the flow volume of blood in the prostate gland for the input information. The various sorts of input information described above may be suitably combined and used for the purpose of setting the therapeutic conditions.

The relational expressions (1-1) and (1-2) used for computing the Experiments 1–3 in setting the therapeutic conditions are valid exclusively under the relevant experimental conditions and are meant solely for illustration. Actually, the relational expressions which are used in the computation for setting the therapeutic conditions must be suitably found empirically, in accordance with the kind and the scale of the thermotherapy to be applied.

The laser beam emitting device in the apparatus for thermotherapy does not need to be limited to the construction illustrated in FIG. 3. Various laser beam emitting devices are usable. For example, a laser beam emitting device which effects necessary thermotherapy by inserting a continuous inserting part into the living body and emitting the laser beam from an emitting part disposed on the inserting part toward the vital tissue and a laser beam emitting device which fulfills necessary thermotherapy by pressing a pressing part to the prostate gland itself or to the vital tissue in the proximity of the prostate gland after the fashion of a surgical operation or pressing a pressing part on the body surface and emitting the laser beam from an emitting part disposed in the pressing part toward the prostate gland may be suitably used.

Figure 16:
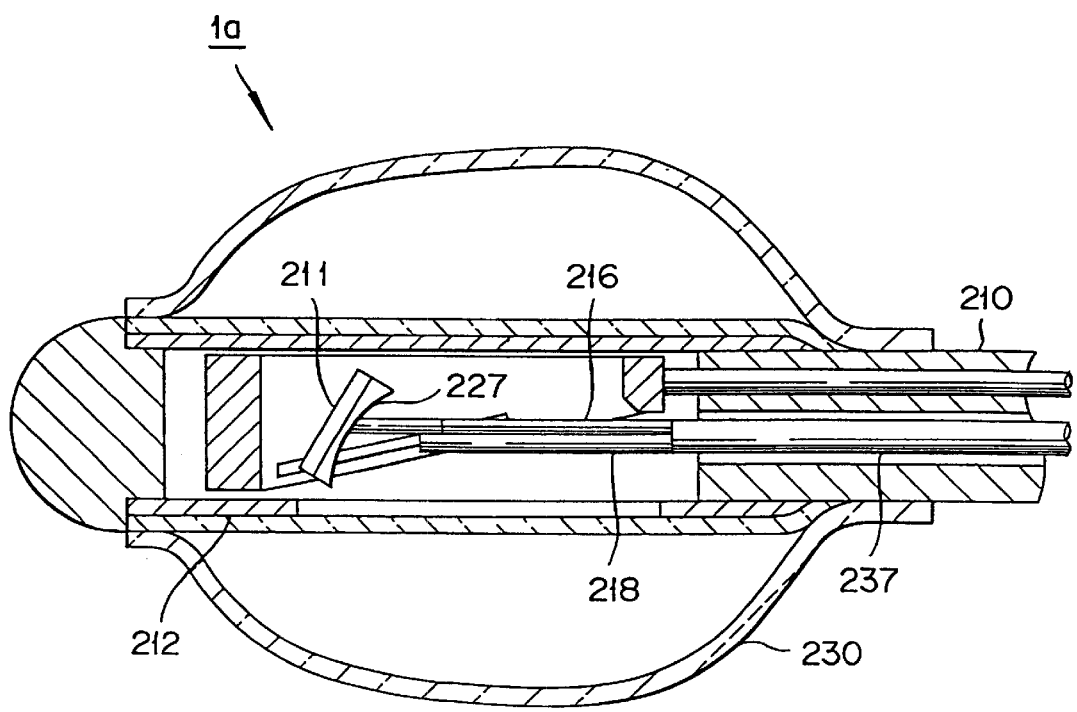
FIG. 16 is a cross section of another example of the leading terminal part of the device for emitting a laser beam.

FIG. 16 is a cross section of the leading terminal part of another example of the laser beam emitting device. The common points between this laser bean emitting device and that of FIG. 3 will be omitted from the following description and the main different points found therebetween will be explained. This laser beam emitting device 1a is provided with an emitting part 211 possessed of a concave reflecting surface 227 for reflecting the laser beam. The laser beam which is transmitted through an optical fiber 218 is converged. The optical fiber 218 and an arm 216 are inserted in a tube 237 and mutually fixed therein. Since the optical fiber 218 and the arm 216, therefore, are jointly reciprocated, the leading terminal of the optical fiber 218 which is irradiated with the laser beam constantly keeps a fixed distance from the reflecting surface 227 and the laser beam constantly maintains its shape.

The laser beam emitting device 1a is further provided with a balloon 230 which is inflated or contracted. The balloon 230 encircles the periphery of a housing 212 which is disposed in the leading terminal part of the main body 210. The balloon 230 is preferred to be formed of such a material as polyolefin, polyester, polyamide, latex, or cellulose which excels in perviousness to the laser beam. The material proves preferable because it is capable of allaying the energy absorbed by the balloon 230 during the passage of the laser beam through the balloon 230 and the temperature rise caused by the absorbed energy. The fluid for inflating the balloon 230 is supplied by utilizing the lumen for injecting and discharging the refrigerant. The lumen is connected at one terminal via a connector (not shown) to the tube for injecting or discharging the refrigerant to and from the refrigerant circulating device 4, and at the other terminal to the balloon 230. The temperature of the refrigerant or the working fluid does not need to be particularly limited but is only required to be capable of cooling the surface layer of the vital tissue. It is properly not more than 37° C. and preferably in the approximate range of 0–25° C. and more preferably in the approximate range of 0–10° C. When the working fluid is a refrigerant, it is preferably circulated to improve the efficiency of cooling. The construction of the apparatus may not allow circulation of the refrigerant. The inflation of the balloon 23 fixes the position and the direction of the laser beam emitting device 1a. Further, since the part which contact the balloon 230 and the proximal areas, namely the surface layer of the vital tissue, are further cooled by the working fluid, the damage to the surface layer can be prevented more infallibly.

Figure 17:
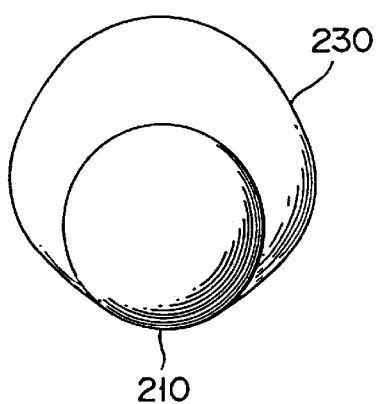
FIG. 17 is a diagram of the device for emitting a laser beam provided with a balloon as viewed from the leading terminal side thereof.

Since the inflation of the balloon 230 results in expanding the urethra 22, the laser beam emitting part changes the distance thereof from the surface of the surface layer 21 of the vital tissue 20. The diameter of the prostate gland, for example, which is found in advance by diagnostic examination of a patient, may be corrected in consideration of the diameter of the balloon in the inflated state. The balloon 230, when necessary, may be formed so as to encircle the entire periphery of the housing 212 except the window part for emission of the laser beam as illustrated in FIG. 17. In this case, the correction of the diameter of the prostate gland found in advance by the diagnostic examination of the patient does not need to be corrected because the inflation of the balloon 230 fixes the distance between the emitting terminal which is the window part of the main body 210 for emitting the laser beam and the emitting part.

Figure 18:
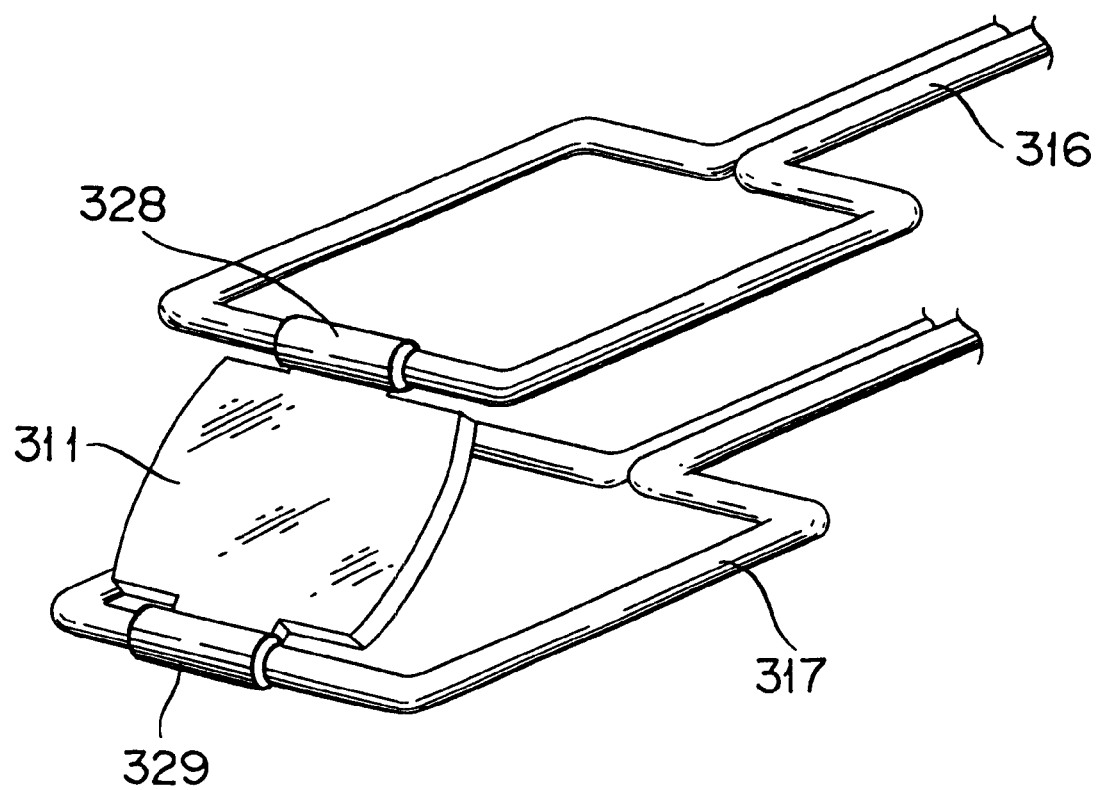
FIG. 18 is a perspective view for explaining another example of the construction of an emitting part and an arm of the device for emitting a laser beam.

Various other types of laser beam emitting device may be used in the place of the laser beam emitting device described above. For example, the emitting part illustrated in FIG. 3 and FIG. 4 is provided on one side thereof with the supporting part 128 and on the other side thereof with the pair of projections 133. In an alternative construction illustrated in FIG. 18, an emitting part 311 is provided on the opposite sides thereof with supporting parts 328 and 329, the supporting parts 328 and 329 are respectively mounted rotatably on separate arms 316 and 317, and the pair of arms 316 and 317 are reciprocated by respective drive units in different strokes in the axial directions, and consequently the emitting part 311 is allowed to have the angle of emission thereof. In this case, since the emitting part is not provided with engaging projections, the grooves otherwise disposed on the inner wall of the housing are no longer necessary. By providing the arms 316 and 317 with adjusters which, although not illustrated, are capable of adjusting the relative lengths thereof, it is made possible to vary the range of variation of the angle of the emitting part 311.

The laser beam emitting device may be so constructed that the position of the laser beam emitting part is fixed in the axial direction during the operation of the device. The laser bean emitting device provided with a fixed emitting part may embrace a modification which is provided with a plurality of emitting parts such that the ranges of emission of laser beam from the respective emitting parts overlap at the site of lesion or a modification which effects emission of the laser beam by transfixing an inserting part containing an emitting terminal into the interior of the prostate gland and emitting the laser beam from the emitting terminal.

The energy projected to the vital tissue, as described herein above, has utilized the laser beam. This invention does not need to be limited thereto but may utilize, for example, a microwave, a radio frequency, or an ultrasound instead.

Now, the apparatus for thermotherapy according to the second mode of embodiment of this invention will be described below.

The apparatus 10 for thermotherapy of the present mode of embodiment is different from that of the first mode of embodiment described above in respect that it is so constructed as to set the therapeutic conditions necessary for the thermotherapy based on the input information including the position information regarding the site of target which is the target site of heating. Since the construction of the apparatus for thermotherapy according to the first embodiment illustrated in FIG. 1–FIG. 9 equals that of the second embodiment, it will be omitted from the following description. The second embodiment will be described herein below as centered around the different points of this mode from the first embodiment.

Figure 19:
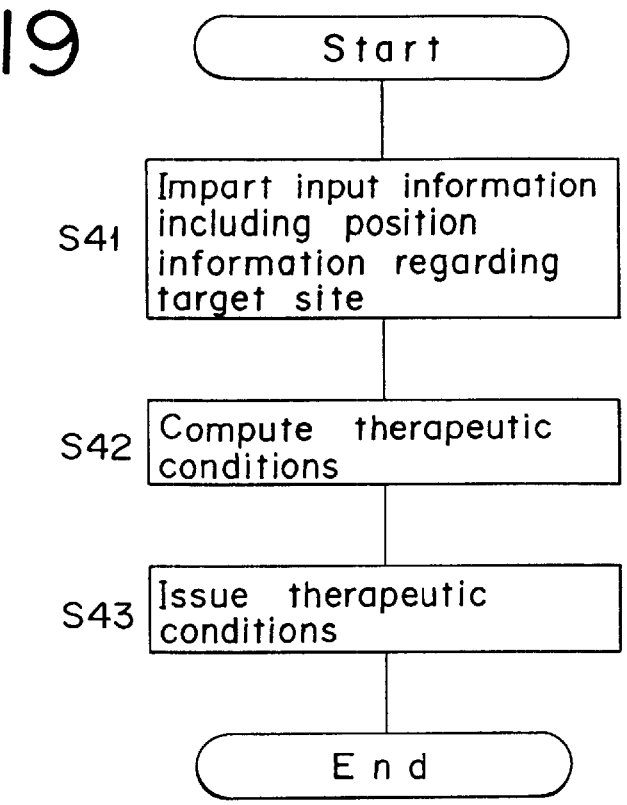
FIG. 19 is a flow chart illustrating a method for setting therapeutic conditions of an apparatus for thermotherapy according to a second embodiment of the invention.

FIG. 19 is a flow chart illustrating a method for setting therapeutic conditions for the apparatus of thermotherapy according to the second embodiment of this invention.

The physician, prior to the use of this apparatus for thermotherapy, determines in advance the site of lesion of a patient diagnostically. The diagnosis of the site of lesion is carried out by the visual examination, the examination using palpation, the examination resorting to percussion and auscultation, the examination with an optical endoscope or ultrasound endoscope, the examination of images by X-ray shadow casting, magnetic resonance imaging (MRI), computed tomography with X ray or magnetic resonance, positron emission tomography (PET), and single photon emission computed tomography (SPECT), and the biopsy, for example.

Next, the physician determines the target site of heating from the site of lesion comprehended by the diagnostic examination and imparts the input information including the position information as an input to the operating part 8 (S41). The expression "position information of the site of target" as used herein refers to the information of the position of the target site in the form of a plane or a space relative to the laser beam emitting device. The controller 6 may be so constructed as to read the input information containing the position information of the target site from the diagnostic data of a patient stored in a memory not shown. The input means does not need to be limited to the operating part 8. For example, the controller 6 may be provided with a device for diagnostically determining the site of lesion not shown or with a connector which, by being connected to an external device such as a computer storing the patient information, is enabled to introduce the position information of the site of target which is the target site of heating from the external device. By using the connecting part mentioned above and consequently enabling the controller 6 to introduce the position information of the target site (which is the target site of heating) during the course of diagnosis or at a time selected arbitrarily by the physician, it is possible to effect automatic setting of the therapeutic conditions, save time and labor in the manipulation of the operating part 8 for the impartation of the input information, and prevent the operating part 8 from admitting erroneous input information.

The controller 6 computes the therapeutic conditions required for effecting the thermotherapy, based on the input information introduced into the operating part 8 (S42). As concrete examples of the therapeutic conditions for the apparatus 10 for thermotherapy, the power of the laser beam, the duration of emission of the laser beam, the temperature of the refrigerant forwarded to the main body 110, the flow volume of the refrigerant forwarded to the main body 110, and the speed of movement of the laser beam emitting part may be cited. Next, the apparatus 10 for thermotherapy automatically computes one or more of these therapeutic conditions. For the computation of the therapeutic conditions, the method which determines the therapeutic conditions by substituting the input information introduced into the operating part 8 for the relevant terms of the relational expressions to be obtained in advance empirically is adopted. The function table which is obtained in advance empirically may be used instead.

Next, the controller 6 issues as an output the therapeutic conditions which have been found by automatic computation (S43). To be specific, the controller 6, depending on the therapeutic conditions found as described above, delivers control signals to the laser beam generating device 2, the drive part electric source 3, the refrigerant circulating device 4, and the refrigerant temperature adjusting device 5. The therapeutic conditions thus determined are displayed on the monitor 7 together with the input information introduced into the operating part 8. Thus, the controller 6 automatically sets the therapeutic conditions required for effecting the thermotherapy, based on the input information introduced into the operating part 8. Here, as the therapeutic conditions which are not automatically set on the basis of the input information, such numerical values as are generally applicable to the thermotherapy are adopted.

The apparatus 10 for thermotherapy, when necessary, may be so constructed that the controller 6 is allowed to issue the control signals to the laser beam generating device 2 and other devices after the monitor 7 has displayed the therapeutic conditions determined by the automatic computation and/or the other therapeutic conditions and the physician has confirmed the therapeutic conditions so displayed and depressed the predetermined switches on the operating part 8 once again. The apparatus may also be so constructed that the therapeutic conditions determined by the automatic computation and/or the other therapeutic conditions may be enabled at this point to receive fine manual adjustment to a certain degree.

In this apparatus 10 for thermotherapy, since the automatic setting of the proper therapeutic conditions is accomplished by simply imparting the input information containing the position information of the site of target (which is the target site of heating) to the apparatus, the physician is no longer required to judge from his own experience numerous items of therapeutic conditions and impart them one by one to the apparatus and consequently enjoys great ease in the procedure for handling the input information. Further, the apparatus is enabled to prevent erroneous therapeutic conditions from being introduced therein. It is, therefore, enabled to heat accurately and easily the site of lesion exclusively in conformity with the morbid state of each patient and meanwhile avoid infliction of damage to the normal tissue in the proximity of the site of lesion.

Figure 20:
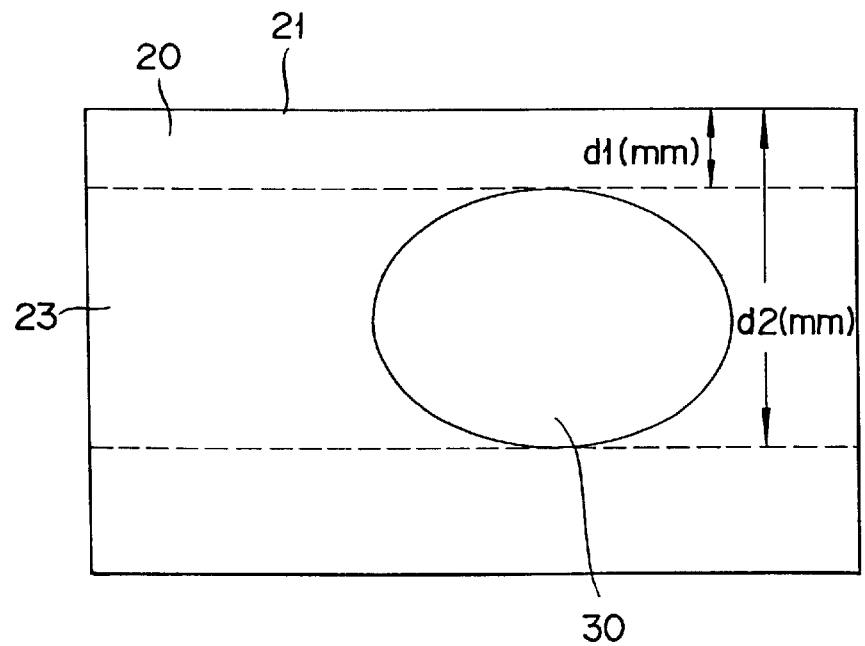
FIG. 20 is a cross section of a vital tissue.

FIG. 20 is a cross section of the vital tissue and FIG. 21 is a flow chart illustrating a method for setting specific therapeutic conditions. The method for setting the therapeutic conditions illustrated in FIG. 21 defines more specifically the therapeutic conditions to be set than the method illustrated in FIG. 19 in that the input information introduced into the operating part 8 is the position information indicating the range in which the temperature of the vital tissue is elevated above a prescribed level. The parts which overlap those described above, therefore, are partly omitted from the following description.

The position information indicating the range in which the temperature of the vital tissue is elevated above a prescribed level pertains to the minimum distance d1 (mm) and the maximum distance d2 (mm) between the emitting terminal 111a which corresponds to the outlet part for emitting the laser beam from the laser beam emitting device 1 to the exterior and the range in which the temperature reaches a prescribed level.

In the case of the laser beam emitting device 1 illustrated in FIG. 1, since the emitting terminal 111a is held in contact with the surface layer 21 of the vital tissue 20, the distances d1 and d2 respectively equal the minimum distance and the maximum distance between the surface of the surface layer 21 and the range in which the temperature surpasses the prescribed level. The range for attaining the temperature surpassing the prescribed level (not less than 45° C., for example, in the case of the prostate gland) generally coincides with the target site 30 which is the target site of heating. The target site 30, as illustrated in FIG. 20, is positioned in the deep part 23 of tissue of the vital tissue 20. It is permissible, however, to adopt a range slightly narrower than the target site 30 as the range for setting the temperature above the prescribed level.

The physician, prior to the use of the apparatus for thermotherapy, first determine the site of lesion of a patient diagnostically. From the site of lesion comprehended by the diagnostic determination, the physician decides the target site 30 which is the target site for heating and imparts as an input into the operating part 8 the distance between the emitting terminal 111a and the range for setting the temperature above the prescribed level, i.e. the minimum distance d1 and the maximum distance d2 to the target site 30 (S51, 52).

The controller 6 automatically computes the power P of the laser beam and the flow volume Q of the refrigerant forwarded to the main body 110 as the therapeutic conditions for effecting the thermotherapy, based on the minimum distance d1 and the maximum distance d2 which have been introduced into the operating part 8 (S53). For the computation of the therapeutic conditions, the method which determines the power P of the laser beam and the flow volume Q of the refrigerant forwarded to the main body 110 by substituting the minimum distance d1 and the maximum distance d2 introduced into the operating part 8 for the relevant terms of the relational expressions determined empirically in advance. Incidentally, as a general trend, the power of the laser beam as the heating factor is set in a higher direction in proportion as the difference (d2−d1) increases or d1 and d2 both increase and the flow volume of the refrigerator as the surface layer cooling factor is set in a larger direction in proportion as d1 and d2 both increase.

Next, the controller 6 issues by way of output the therapeutic conditions found by the automatic computation (S54). To be specific, the controller 6 issues control signals to the laser beam generating device 2 and the refrigerant circulating device 4, depending on the therapeutic conditions found as described above. The therapeutic conditions so determined are displayed on the monitor 7 together with the input information introduced into the operating part 8. Thus, the controller 6 automatically sets the therapeutic conditions required for the thermotherapy, based on the minimum distance d1 and the maximum distance d2 between the emitting terminal 111a and the target site 30 which have been introduced into the operating part 8. Here, as the therapeutic conditions which are not automatically set on the basis of the input information, such numerical values as are generally applicable to the thermotherapy are adopted. The controller 6 issues control signals to the drive part electric source 3 and the refrigerant temperature adjusting device 5, depending on the therapeutic conditions mentioned above.

In accordance with the method for setting the therapeutic conditions illustrated in FIG. 21, by simply imparting as an input the distance from the laser beam emitting terminal 111a to the target site 30, it is possible to set accurately and very easily without committing an error the therapeutic conditions required for effectively heating the site of lesion exclusively in conformity with the morbid state of each patient while avoiding infliction of damage to the normal tissue in the proximity of the site of lesion.

While the method for setting the therapeutic conditions illustrated in FIG. 21, as described above, has described the therapeutic conditions to be automatically set to the power P of the laser beam; and the flow volume of the refrigerant forwarded to the main body 110, this invention is not limited to these therapeutic conditions. For example, the duration of emission of the laser beam, the temperature of the refrigerant forwarded to the main body 110, and the speed of movement of the laser beam emitting part may be enabled to be automatically set by simply imparting as an input the distance ($d_1$, $d_2$) from the laser beam emitting terminal 111a to the target site 30. In this case, the duration of emission of the laser beam as a heating factor is set in a longer direction in proportion as the difference (d2−d1) increases or d1 and d2 both increase, the duration of irradiation of the laser beam as a heating factor is set in a longer direction in proportion as d1 and d2 both increase, and the temperature of the refrigerant as a surface layer cooling factor is set in a lower direction and the speed of movement of the laser beam emitting part is set in a faster direction in proportion as D1 and D2 both increase.

Figure 23:
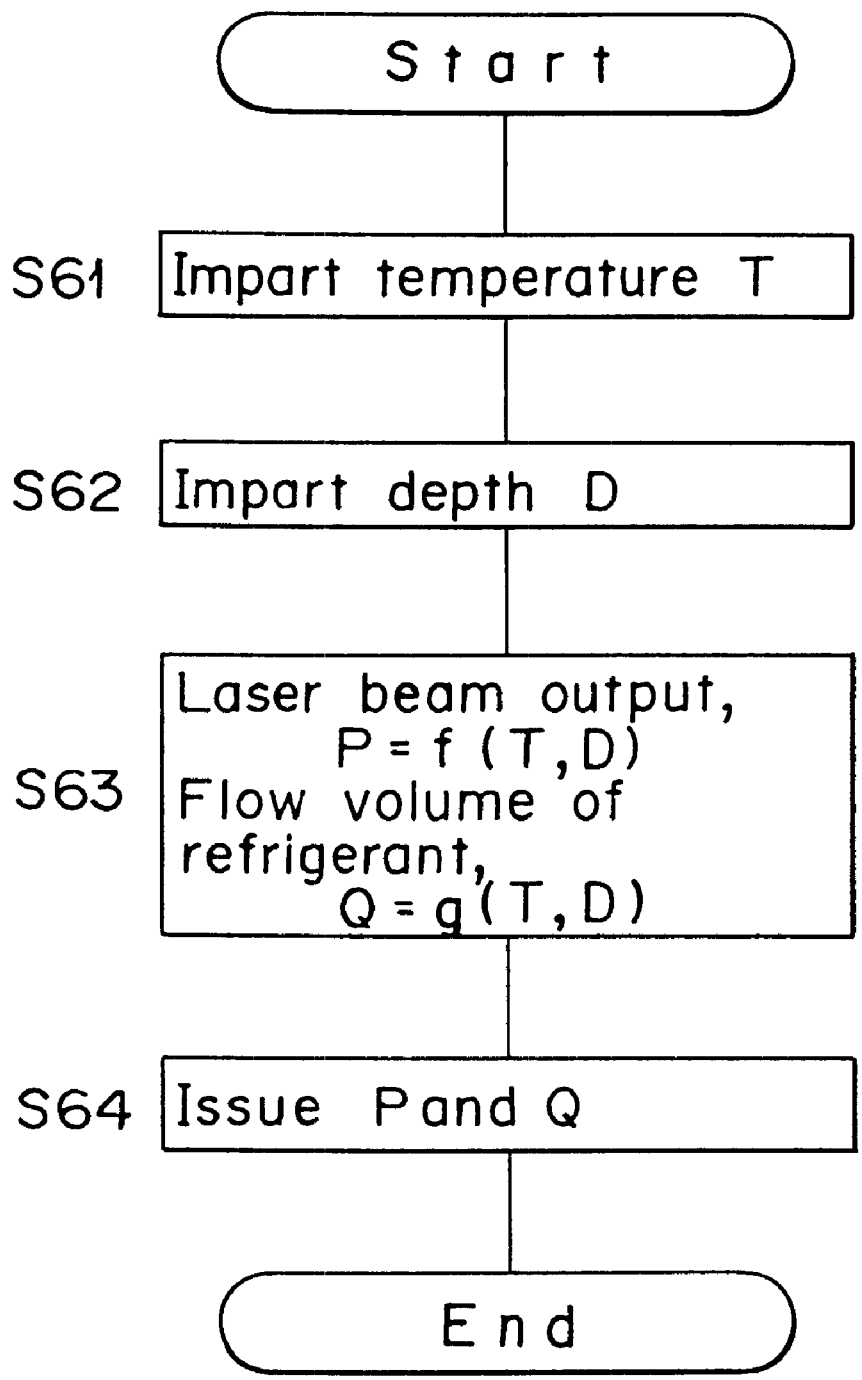
FIG. 23 is a flow chart illustrating another method for setting specific therapeutic conditions.

FIG. 22 is a cross section of the vital tissue and FIG. 23 is a flow chart illustrating another method for setting specific therapeutic conditions.

The method for setting the therapeutic conditions illustrated in FIG. 23 is different from the method for setting the therapeutic conditions illustrated in FIG. 21 in that the input information to be imparted to the operating part 8 pertains to the position information indicating the point at which the temperature of the vital tissue is elevated to the highest level and the temperature information indicating the target temperature at this point. The parts which overlap those described above, therefore, are partly omitted from the following description.

The position information which indicates the point in the vital tissue which is heated to the highest temperature pertains to the distance D (mm) from the laser beam emitting terminal 111a to the point which is heated to the highest temperature. In the case of the laser beam emitting device 1 illustrated in FIG. 1, since the emitting terminal 111a is held in contact with the surface layer 21 of the vital tissue 20, the distance D equals the distance from the surface of the surface layer 21 to the point in the vital tissue which is heated to the highest temperature. The target point 41 can be set at the point which is not deeper than the beam cross point 40.

The physician, prior to the use of the apparatus for thermotherapy, determines in advance the site of lesion of a patient diagnostically. From the diagnosed site of lesion, the physician decides the target site 30 (the target site of heating) and imparts as inputs the distance D (mm) from the emitting terminal 111a to the target point 41 (point in the vital tissue which is heated to the highest temperature), and the target temperature T (°C.) at the target point 41 to the apparatus via the operating part 8 (S61, S62).

The controller 6 automatically computes the power P of the laser beam and the flow volume Q of the refrigerant forwarded to the main body 110 (the therapeutic conditions required for the thermotherapy), based on the distance D and the target temperature T which have been introduced into the operating part 8 (S63). For the computation of the therapeutic conditions, the power P of the laser beam and the flow volume Q of the refrigerant forwarded to the main body 110 are determined by substituting the temperature T and the distance D introduced into the operating part 8 for the relevant terms of the relational expressions found empirically in advance. Incidentally, as a general trend, the power of the laser beam as a heating factor is set higher and the flow volume of the refrigerant as a surface layer cooling factor is set larger in proportion as D and T increase.

Next, the controller 6 issues as an output the therapeutic conditions which have been found by automatic computation (S64). To be specific, the controller 6 issues control signals to the laser beam generating device 2 and the refrigerant circulating device 4, in conformity with the therapeutic conditions obtained as described above. The therapeutic conditions thus obtained are displayed on the monitor 7 together with the input information introduced into the operating part B. Thus, the controller 6 automatically sets the therapeutic conditions required for the thermotherapy, based on the distance D from the emitting terminal 111a to the target point 41 and the target temperature T at the target point 41 which have been introduced as an input to the operating part 8. Here, as the therapeutic conditions which are not automatically set on the basis of the input information, such numerical values as are generally applicable to the thermotherapy are adopted. The controller 6 issues control signals to the drive part electric source 3 and the refrigerant temperature adjusting device 5, depending on the therapeutic conditions mentioned above.

In accordance with the method for setting the therapeutic conditions illustrated in FIG. 23, by simply imparting as an input the distance D from the laser beam emitting terminal 111a to the target point 41 and the target temperature T at the target point 41, it is made possible to set accurately and very easily without committing an error the therapeutic conditions required for effectively heating the site of lesion exclusively in conformity with the morbid state of each patient while avoiding infliction of damage to the normal tissue in the proximity of the site of lesion.

The method for setting the therapeutic conditions illustrated in FIG. 23, as described above, limits the therapeutic conditions to be automatically set to the power P of the laser beam and the flow volume Q of the refrigerant forwarded to the main body 110. This invention does not need to adhere to this limitation. For example, the duration of emission of the laser beam, the temperature of the refrigerant forwarded to the main body 110, and the speed of movement of the laser beam emitting part may be enabled to be automatically set by simply imparting as an input the distance D from the laser beam emitting terminal 111a to the target point 41 and the target temperature T at the target point 41.

Figure 24:
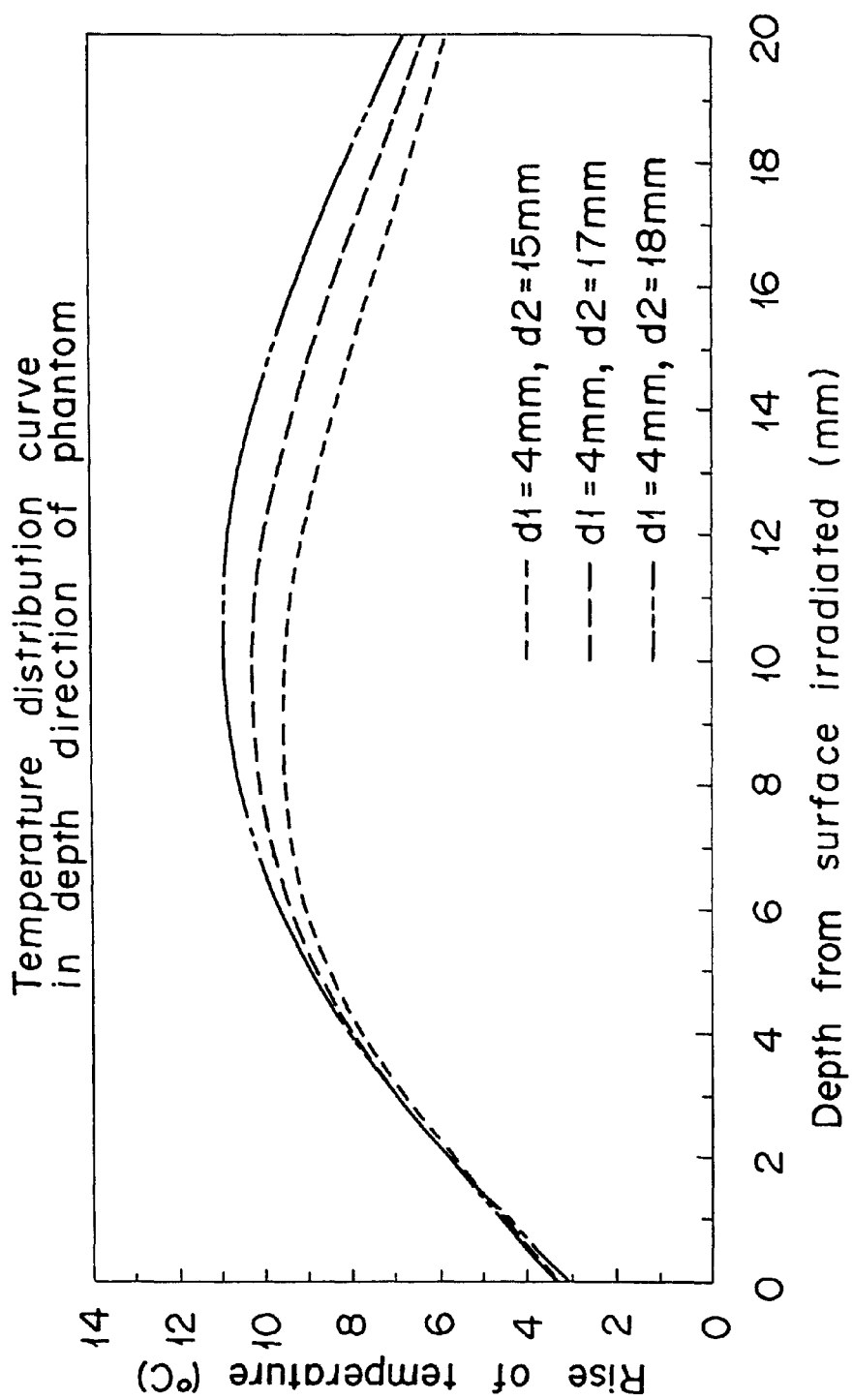
FIG. 24 and FIG. 25 are diagrams illustrating the results of an experiment for measuring temperature distribution of a tissue heated by using the method for setting therapeutic conditions illustrated in FIG. 21, and FIG. 26 through FIG. 28 are diagrams illustrating the results of experiments of measuring temperature distribution of a tissue heated by using the method for setting therapeutic conditions illustrated in FIG. 23.
Figure 25:
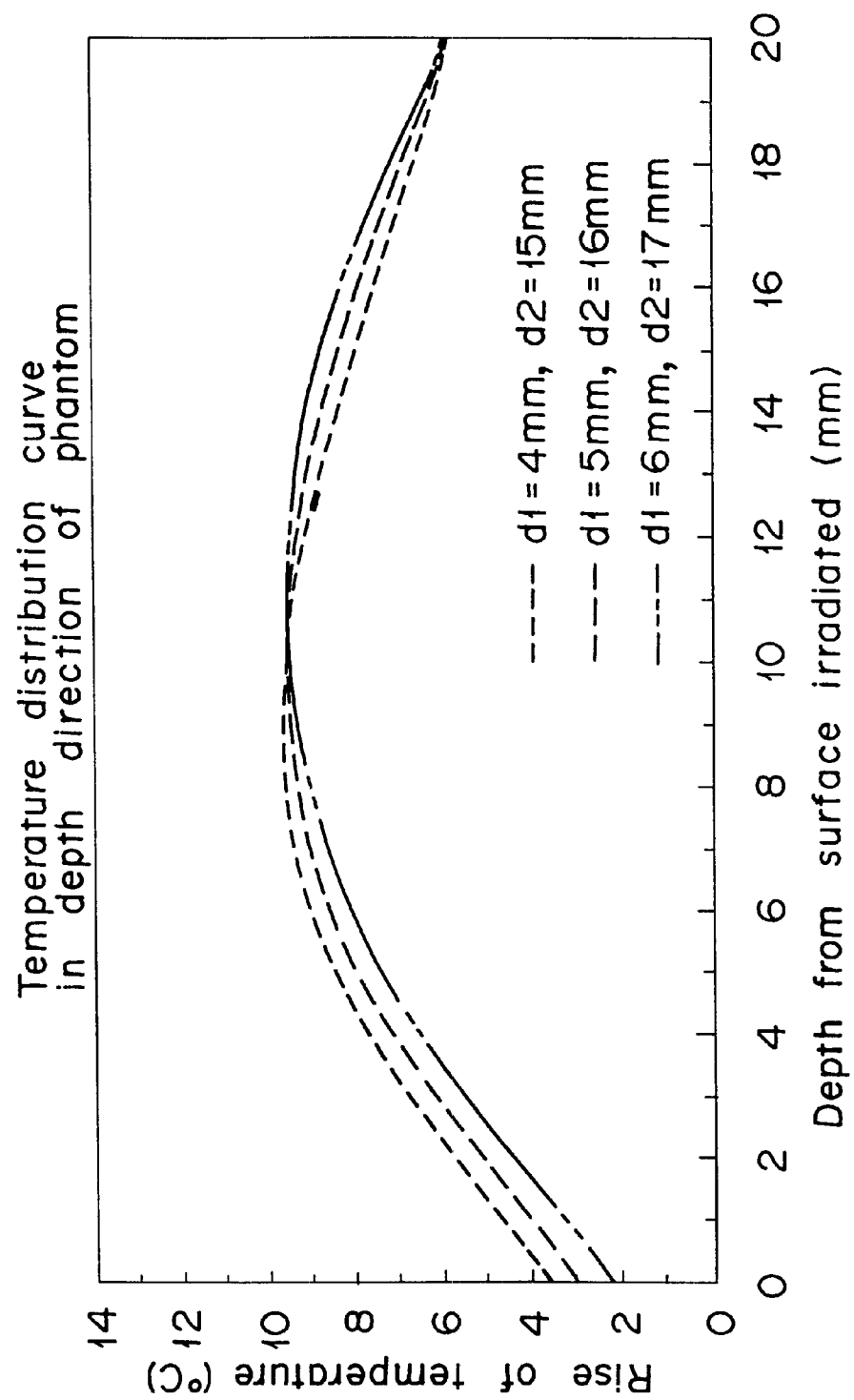

FIG. 24 and FIG. 25 are diagrams illustrating the results of the experiment of measuring the temperature distribution in the tissue heated by using the method for setting the therapeutic conditions illustrated in FIG. 21.

The experiment regarding FIG. 24 and FIG. 25 was carried out by using the apparatus 10 for thermotherapy illustrated in FIG. 1. In the laser beam emitting device 1 used in the experiment, however, the arm 116 and the optical fiber 118 are fixed in the proximity of the leading terminal of the optical fiber and the arm 116 and the optical fiber 118 are jointly moved and the main body 110 is provided at the leading terminal part thereof with a balloon capable of cooling the surface of the tissue irradiated with the laser beam (similarly in the balloon 230 of FIG. 16). This balloon has an outside diameter of 8 mm in the inflated state.

The experiment was carried out under the following conditions.

Object for heating: Chicken (as phantom)

Laser beam: Wavelength 810 nm, continuous wave, beam diameter on the surface of tissue 4 mm, numerical aperture NA=0.26

Ambient Temperature: Room temperature 22° C.

Duration of heating (duration of emission of laser beam): 15 minutes

Temperature of refrigerant: 22° C.

Speed of movement of laser beam emitting part: 3 reciprocations/second

Length of movement of laser beam emitting part: 20 mm

Distance from the emitting terminal to the beam cross point: 15 mm

Temperature set for heating: Room temperature +8° C.

The relational expressions empirically obtained in advance to be used for finding the power P (W) of the laser beam and the flow volume Q (ml/min) of the refrigerant forwarded to the main body 110 from the minimum distance d1 (mm) and the maximum distance d2 (mm) are as follows.

Where $d1=4$ and $15 \leq d2 \leq 18$;

$$P = A1 \cdot (d2-4)^2 - B1 \cdot (d2-4) + C1 \qquad (2\text{-}1)$$

$$Q = A2 \cdot (d2-4)^2 - B2 \cdot (d2-4) + C2 \qquad (2\text{-}2)$$

wherein
A1=0.1333, B1=2.8, and C1=23.17 and
A2=8.3333, B2=175, and C2=967

Where $4 < d1 \leq 6$ and $d2 - d1 = 11$;

$$P = D1 + E1 \cdot (d1-4) \qquad (2\text{-}3)$$

$$Q = D2 + E2 \cdot (d1-4) \qquad (2\text{-}4)$$

wherein
D1=8.5 and E1=0.25
D2=50 and E2=75

FIG. 24 and FIG. 25 pertain to five experiments, i.e. Experiment 1a: d1=4 and d2=15, Experiment 2a: d1=4. and d2=17, Experiment 3a: d1=4 and d2=18, Experiment 4a: d1=5 and d2=16, and Experiment 5a: d1=6 and d2=17. By imparting as an input the minimum distance d1 (mm) and the maximum distance d1 (mm) from the surface of the tissue to the target site 30 obtained in Experiments 1a–5a into the operating part 8 of the apparatus 10 for thermotherapy, it is enabled to set the power P (W) of the laser beam and the flow volume Q (ml/min) of the refrigerant forwarded to the main body 110 as follows in accordance with the expressions (2-1)–(2-4) mentioned above.

Specifically, Experiment 1a: P=8.5 and Q=50, Experiment 2a: P=9.3 and Q=100, Experiment 3a: P=10.1 and Q=150, Experiment 4a: P=8.8 and Q=125, and Experiment 5a: P=9.0 and Q=200 are obtained.

The object for heating was heated under the therapeutic conditions set as described above and the temperature distribution in the heated object was measured to a depth of 20 mm from the surface of the object. The results of the experiments 1a–3a are shown in FIG. 24 and those of the experiments 1a, 4a, and 5a in FIG. 25.

By referring to FIG. 24 and FIG. 25, it is clearly noted that the present apparatus for thermotherapy enabled exclusively the target site existing in the range from the minimum distance d1(mm) to the maximum distance d2 to be accurately and easily heated to a level above the target heating temperature (elevated temperature +8° C.).

Figure 26:
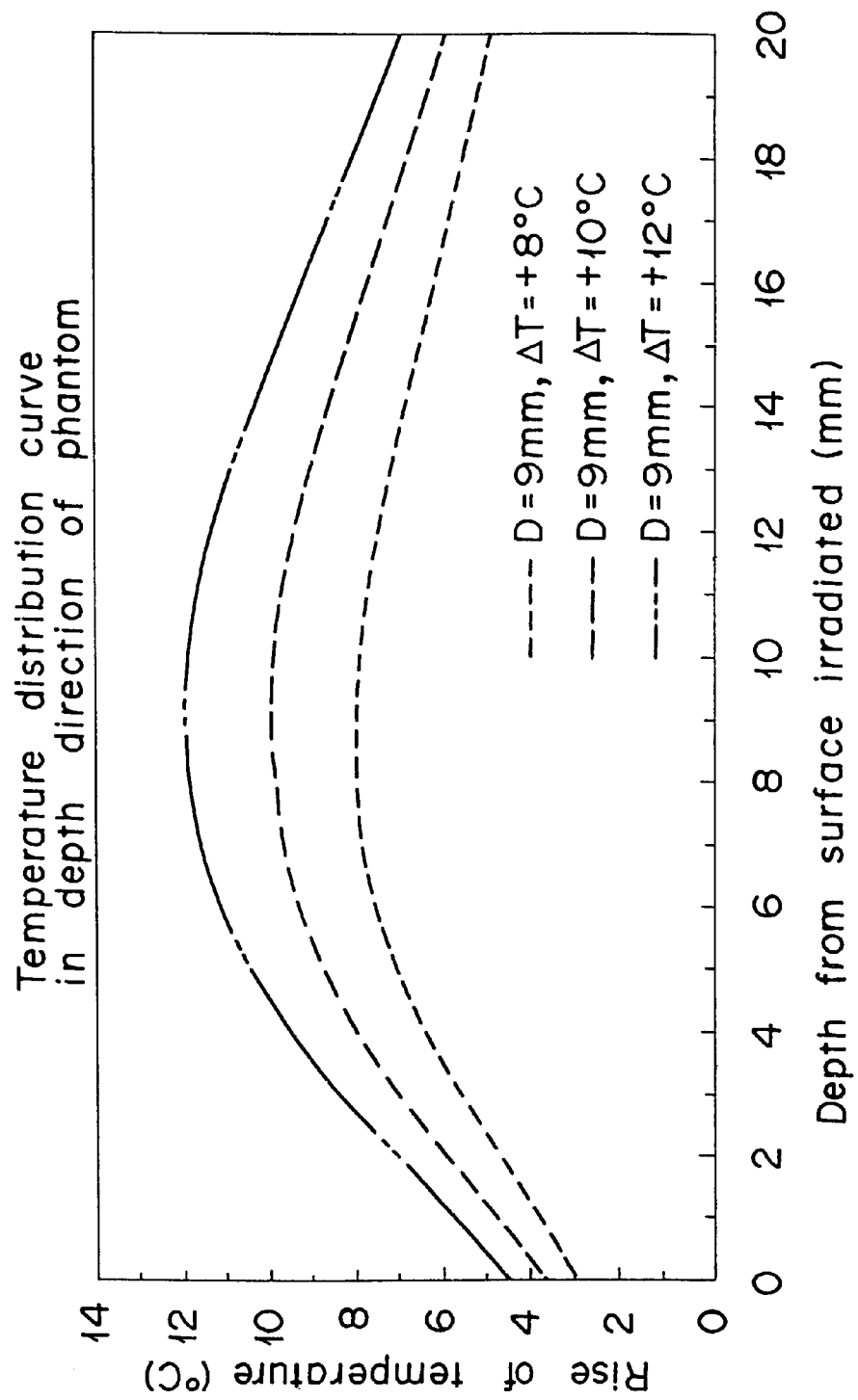

FIG. 26–FIG. 28 are diagrams illustrating the results of the experiment of measuring the temperature distribution in the tissue heated by using the method for setting the therapeutic conditions as illustrated in FIG. 23.

The experiments concerning FIG. 26–FIG. 28 used the same apparatus for thermotherapy as the apparatus used in the experiments concerning FIG. 24 and FIG. 25.

These experiments were carried out under the following conditions.

Object for heating: Chicken (as phantom)

Laser beam: Wavelength 810 nm, continuous wave, beam diameter on the surface of tissue 4 mm, numerical aperture NA=0.26

Temperature of ambience: Room temperature 22° C.

Duration of heating (duration of emission of laser beam): 15 minutes

Temperature of refrigerant: 22° C.

Speed of movement of laser beam emitting part: 3 reciprocations/second

Length of movement of laser beam emitting part: 20 mm

Distance from the emitting terminal to the beam cross point: 15 mm

The relational expressions empirically obtained in advance to be used for finding the power P (W) of the laser beam and the flow volume Q (ml/min) of the refrigerant forwarded to the main body 110 from the distance D (mm) from the surface of the tissue to the target point and the target temperature T (°C.) at the target point are as follows.

Where $+8 \leq \Delta T \leq +12$ and $9 \leq D \leq 11$;

$$P = F \cdot \Delta T + G + (H \cdot \Delta T - I) \times (D-9) \quad (3\text{-}1)$$

$$Q = J + K \times (D-9) \quad (3\text{-}2)$$

wherein F=0.825, G=0.5, H=0.05, I=0.2, J=50, and K=75

The expressions mentioned above require introduction of the value of rise of the target temperature $\Delta T$ (°C.). Where the target temperature T (°C.) is used for the input information, the expression (3-1) mentioned above is substituted for the following expression (3-3) wherein T0 (°C.) denotes the temperature of the tissue under treatment. In this case, the temperature T0 of the tissue under treatment is measured separately and imparted as an input through the operating part 8.

Where $+8 \leq T-T0 \leq +12$ and $9 \leq D < 11$;

$$P = F \times (T-T0) + G + (H \times (T-T0) - I) \times (D-9) \quad (3\text{-}3)$$

FIG. 26–FIG. 28 pertain to seven experiments, i.e. Experiment 1b: $\Delta T=+8$ and D=9, Experiment 2b: $\Delta T=+10$ and D=9, Experiment 3b: $\Delta T=+12$ and D=9, Experiment 4b: $\Delta T=+8$ and D=10, Experiment 5b: $\Delta T=+8$ and D=11, Experiment 6b: $\Delta T=+12$ and D=10, and Experiment 7b: $\Delta T=+12$ and D=11. By imparting as an input the distance D (mm) from the emitting terminal 111a to the target point and the target temperature (°C.) or the value of rise of the target temperature $\Delta T$ (°C.) at the target point obtained in Experiments 1b–7b into the operating part 8 of the apparatus 10 for thermotherapy, it is enabled to set the power P (W) of the laser beam and the flow volume Q (ml/min) of the refrigerant forwarded to the main body 110 as follows in accordance with the expressions (3-1)–(3-3) mentioned above.

Specifically, Experiment 1b: P=7.1 and Q=50, Experiment 2b: P=8.8 and Q=50, Experiment 3b: P=10.4 and Q=50, Experiment 4b: P=7.3 and Q=125, and Experiment 5b: P=7.5 and Q=200, Experiment 6b: P=10.8 and Q=125, and Experiment 7b: P=11.2 and Q=200 are obtained.

The object for heating was heated under the therapeutic conditions set as described above and the temperature distribution in the heated object was measured to a depth of 20 mm from the surface of the object. The results of the experiments 1b–3b are shown in FIG. 26, those of the experiments 1b, 4b, and 5b in FIG. 27 and those of the experiments 3b, 6b, and 7b in FIG. 28.

By referring to FIG. 26–FIG. 28, it is clearly noted that the present apparatus for thermotherapy enabled exclusively the point in the vital tissue which was heated to the highest temperature, namely the target point existing at the distance D from the surf ace of the tissue, to be accurately and easily heated as indicated by the value $\Delta T$ (°C.) of the rise in the target temperature.

The apparatus of this invention for thermotherapy is preferably applied to the thermotherapy of such diseases of the prostate gland as the benign prostatic hyperplasia and the cancer of the prostate gland, wherein the interior of the prostate gland is exclusively heated to a predetermined temperature without heating the normal tissue of the urethra and the rectum existing in the proximity of the prostate gland to a level above the predetermined temperature.

The apparatus for thermotherapy according to this mode of embodiment, as described above, has used the minimum distance and the maximum distance from the laser beam emitting terminal to the target site and the distance to the point in the target site which reaches the highest temperature as the position information as to the target site which is the target site of heating. This invention does not need to adhere to this limitation. It is otherwise allowable to use the distance from the laser beam emitting terminal to the central point in the target site and the width in the direction of width for the position information relating to the target site.

The relational expressions (2-1)–(2-4) and (3-1)–(3-3) used for the computation performed in the Experiments 1a–5a and 2b–7b for setting the therapeutic conditions are valid exclusively under the relevant experimental conditions and are meant solely for illustration. Actually, the relational expressions which are used in the computation for setting the therapeutic conditions must be suitably found empirically, in accordance with the kind and the scale of the thermotherapy to be applied.

When the laser beam emitting device to be used is provided with such a balloon as illustrated in FIG. 16, since the inflation of the balloon 230 results in expanding the vital tissue, the laser beam emitting part changes the distance thereof from the surface of the surface layer 21 of the vital tissue 20. It is, therefore, commendable to correct the position information of the target site 30 obtained in advance by diagnostically examining the site of lesion of an experiment by taking into consideration the diameter of the balloon in the inflated state. The balloon 230, when necessary, may be so formed as to encircle the entire periphery of the housing 212 except the window part for emitting the laser beam as illustrated in FIG. 17. In this case, since the inflation of the balloon 230 fixes the distance between the emitting terminal which is the window part in the main body 210 for emitting the laser beam and the emitting part, the physician is no longer required to correct the position information of the target site 30 obtained in advance by the diagnostic examination of the site of lesion of a patient.

This invention does not need to be limited to the specific examples of the mode of embodiment described above but may be altered or amended variously without departure from the technical concept of this invention.

This application is based on applications No. 11-199,672 and No. 11-199,673 filed in Japan, the contents of which are hereby incorporated by reference.

What is claimed is:

1. An apparatus for thermotherapy of prostate gland comprising:

an energy generating device for generating energy;

an emitting part for directing the energy generated by said energy generating device to a vital tissue to irradiate the vital tissue;

an input part for imparting, as an input, information containing diagnostic data of said prostate gland;

a control part for setting therapeutic conditions on the basis of the input information and controlling the operation of said energy generating device on the basis of the therapeutic conditions;

moving means for moving the emitting part in a direction with respect to the vital tissue irradiated with the energy; and interlocking means for altering an angle of irradiation of the emitting part in accordance with the movement of the emitting part.

2. The apparatus according to claim 1, which further comprises a long and slender inserting part intended for insertion into a living body, wherein the emitting part is disposed in the inserting part.

3. An apparatus according to claim 1, wherein said input information includes the diameters of said prostate gland in three respective axial directions.

4. An apparatus according to claim 1, wherein said energy is a laser beam.

5. An apparatus according to claim 1, wherein said therapeutic conditions are one or more therapeutic conditions selected from the group consisting of the power of said energy, the duration of emission of said energy, the temperature of a refrigerant, if any used herein, and the flow volume of said refrigerant where said refrigerant is circulated for required service.

6. An apparatus for thermotherapy of prostate gland comprising:

an energy generating device for generating energy;

an emitting part for directing the energy generated by said energy generating device to the vital tissue to irradiate the vital tissue;

an input part for imparting, as an input, information containing data specifying a size of said prostate gland;

a control part for setting therapeutic conditions on the basis of the input information and controlling operation of said energy generating device on the basis of the therapeutic conditions;

moving means for moving the emitting part with respect to the surface of the vital tissue irradiated with the energy; and interlocking means for altering an angle of irradiation of the emitting part in accordance with the movement of the emitting part.

7. An apparatus according to claim 6, wherein said input part acquires the data stored in a device other than the apparatus for thermotherapy by means of an electronic circuit.

8. The apparatus according to claim 6, wherein said thermotherapy is prohibited when said data is smaller than a minimum characteristic value set in advance.

9. The apparatus according to claim 6, wherein said data is substituted for a maximum characteristic value set in advance and said therapeutic conditions are set accordingly when said data is larger than the maximum characteristic value.

10. The apparatus according to claim 6, wherein said therapeutic conditions are set based on a smallest of at least two kinds of data.

11. An apparatus for thermotherapy of affected vital tissue comprising:

an energy generating device for generating energy;

an emitting part for directing the energy generated by said energy generating device to the vital tissue to irradiate the vital tissue;

an input part for imparting, as an input, information containing position information regarding a target site of heating;

a control part for setting therapeutic conditions on the basis of the input information and controlling operation of said energy generating device on the basis of the therapeutic conditions;

moving means for moving the emitting part with respect to the surface of the vital tissue irradiated with the energy; and interlocking means for altering an angle of irradiation of the emitting part in accordance with the movement of the emitting part.

12. The apparatus according to claim 11, comprising:

a long and slender part intended for insertion into the living body; and the emitting part disposed in said inserting part and adapted to direct the energy toward the vital tissue.

13. An apparatus according to claim 11, wherein said input part acquires the data stored in a device other than said apparatus for thermotherapy by means of an electronic circuit.

14. The apparatus according to claim 11, wherein said input information includes position information indicating a range of the vital tissue to be heated to a level exceeding a prescribed level.

15. The apparatus according to claim 11, wherein said input information includes position information indicating a point in the vital tissue to be heated to a highest temperature and temperature information indicating a target temperature at said point.

16. The apparatus according to claim 11, wherein said energy is a laser beam.

17. The apparatus according to claim 11, wherein said therapeutic conditions are one or more therapeutic conditions selected from the group consisting of a power of said energy, a duration of emission of said energy, a temperature of a refrigerant, and a flow volume of said refrigerant where said refrigerant is circulated for required service.

18. An apparatus for thermotherapy of affected vital tissue comprising:

an energy generating device for generating an energy;

an irradiating part for directing the energy generated by said energy generating device to a vital tissue to irradiate the vital tissue;

an input part for imparting as an input information containing the position information regarding a target site of heating; and a control part for setting therapeutic conditions on the basis of the input information and controlling the operation of said energy generating device on the basis of the therapeutic conditions, wherein said input information includes position information indicating a point in the vital tissue to be heated to a highest temperature and temperature information indicating the target temperature at said point.

* * * * *